United States Patent
Liu et al.

(10) Patent No.: US 11,208,482 B2
(45) Date of Patent: Dec. 28, 2021

(54) HUMANIZED ANTIBODIES AGAINST C-KIT

(71) Applicant: Forty Seven, Inc., Menlo Park, CA (US)

(72) Inventors: Jie Liu, Menlo Park, CA (US); Kavitha Sompalli, Menlo Park, CA (US)

(73) Assignee: FORTY SEVEN, INC., Foster City, CA (US)

( * ) Notice: Subject to any disclaimer, the term of this patent is extended or adjusted under 35 U.S.C. 154(b) by 247 days.

(21) Appl. No.: 16/694,975

(22) Filed: Nov. 25, 2019

(65) Prior Publication Data

US 2020/0165337 A1    May 28, 2020

Related U.S. Application Data

(60) Provisional application No. 62/771,526, filed on Nov. 26, 2018.

(51) Int. Cl.
*C07K 16/00* (2006.01)
*C07K 16/28* (2006.01)

(52) U.S. Cl.
CPC ...... *C07K 16/2803* (2013.01); *C07K 2317/24* (2013.01); *C07K 2317/565* (2013.01); *C07K 2317/732* (2013.01)

(58) Field of Classification Search
None
See application file for complete search history.

(56) References Cited

U.S. PATENT DOCUMENTS

| | | | |
|---|---|---|---|
| 5,821,108 A | 10/1998 | Akashi et al. | |
| 6,881,557 B2 | 4/2005 | Foote | |
| 7,915,391 B2 | 3/2011 | Ng et al. | |
| 8,361,736 B2 | 1/2013 | Majeti et al. | |
| 8,436,150 B2 | 5/2013 | Ng et al. | |
| 8,552,157 B2 * | 10/2013 | Amatulli | A61K 33/243 530/388.24 |
| 8,562,997 B2 | 10/2013 | Jaiswal et al. | |
| 8,709,429 B2 | 4/2014 | Majeti et al. | |
| 8,791,249 B2 | 7/2014 | Ng et al. | |
| 9,193,955 B2 | 11/2015 | Majeti et al. | |
| 9,399,682 B2 | 7/2016 | Jaiswal et al. | |
| 9,493,575 B2 | 11/2016 | Jaiswal et al. | |
| 9,605,076 B2 | 3/2017 | Jaiswal et al. | |
| 9,611,329 B2 | 4/2017 | Jaiswal et al. | |
| 9,624,305 B2 | 4/2017 | Jaiswal et al. | |
| 9,765,143 B2 | 9/2017 | Jaiswal et al. | |
| 9,796,781 B2 | 10/2017 | Majeti et al. | |
| 9,932,419 B2 | 4/2018 | LaFleur et al. | |
| 10,072,091 B2 | 9/2018 | Weissman et al. | |
| 10,406,179 B2 | 9/2019 | Shizura et al. | |
| 11,041,022 B2 | 6/2021 | Liu et al. | |
| 2007/0253951 A1 | 11/2007 | Ng et al. | |
| 2012/0253017 A1 | 10/2012 | Ballard et al. | |
| 2012/0283124 A1 | 11/2012 | Park et al. | |
| 2017/0081421 A1 | 3/2017 | Harms et al. | |
| 2018/0155405 A1 | 6/2018 | Ring et al. | |
| 2018/0214524 A1 | 8/2018 | Weissman et al. | |
| 2019/0100593 A1 | 4/2019 | Scadden et al. | |
| 2020/0369767 A1 | 11/2020 | Gibbs et al. | |

FOREIGN PATENT DOCUMENTS

| | | |
|---|---|---|
| EP | 2010571 B1 | 10/2018 |
| WO | WO 2007/127317 A2 | 11/2007 |
| WO | WO 2008/067115 A2 | 6/2008 |
| WO | WO 2009/091547 A1 | 7/2009 |
| WO | WO 2009/091601 A1 | 7/2009 |
| WO | WO 2011/034969 A1 | 3/2011 |
| WO | WO 2011/143624 A2 | 11/2011 |
| WO | WO 2013/109732 A2 | 7/2013 |
| WO | WO-2014/018625 A1 | 1/2014 |
| WO | WO 2014/049477 A1 | 4/2014 |
| WO | WO 2016/033201 A1 | 3/2016 |
| WO | WO 2016/179399 A1 | 11/2016 |
| WO | WO 2017/181033 A1 | 10/2017 |
| WO | WO 2018/140940 A1 | 8/2018 |
| WO | WO 2018/237168 A1 | 12/2018 |
| WO | WO 2019/023347 A1 | 1/2019 |
| WO | WO 2020/112687 A2 | 6/2020 |
| WO | WO 2020/112870 A1 | 6/2020 |

OTHER PUBLICATIONS

U.S. Appl. No. 62/771,526, filed Nov. 26, 2018, n/a, Expired.
PCT/US2019/063091, filed Nov. 25, 2019, WO 2020/112687, Published.
Ahmadzadeh, et al., "Antibody Humanization Methods for Deveopment of Therapeutic Applications," Monoclonal Antibodies in Immunodiagnosis and Immunotherapy, vol. 33, No. 2, (2014).
Antibody Engineering Methods and Protocols, Second Edition, INSERM U624, Antibody Therapeutics & Immunotageting, Marseille, France, edited by Patrick Chame, Humana Press, (2012).
Choi, et al., "Antibody umanization by structure-based computational protein design," mAbs, 7:6, 1045-1057, doi: 10.1080/19420862.2015.107660, (2015).
Choi, et al., "Computationally driven antibody engineering enables simultaneous humanization and thermostabilization," Protein Engineering, Design & Selection, vol. 29, No. 10, pp. 419-426, (2016).
Hanf, et al., "Antibody humanization by redesign of complementarity-determining region residues proximate to the acceptor framework," Methods, 65, 68-76, (2014).
Margreitter, et al., "Antibody humanization by molecular dynamics simulations—in-silico guided selection of critical backmutations," J. Mol. Recongnit., 29: 266-275, (2016).
Safdari, et ai., "Antibody humanization methods—a review and update," Biotechnology and Genetic Engineering Reviews, vol. 29, No. 2, 175-186, (2013).

(Continued)

*Primary Examiner* — Meera Natarajan

(57) ABSTRACT

The invention provides antibodies specifically binding to c-Kit and methods of using such antibodies in stem cell replacement and treatment of cancer.

10 Claims, 15 Drawing Sheets

Specification includes a Sequence Listing.

(56) References Cited

OTHER PUBLICATIONS

Voets, et al., Functional characterization of the selective pan-allele anti-siRPα antibody ADU-1805 that blocks the SIRPα-CD47 innate immuune checkpoint,: Journal for ImmunoTherapy of Cancer, Voll 7:340, pp. 1-15, (Dec. 4, 2019).
WIPO Application No. PCT/US2019/063091 , PCT International Search Report and Written Opinion of the International Searching Authority dated Jul. 14, 2020.
WIPO Application No. PCT/US2020/034049 PCT International Search Report and Written Opinion of the International Searching Authority dated Sep. 3, 2020.
Intl. Preliminary Report on Patentability-Written Opinion dated Jun. 10, 2021 for Intl. Appl. No. PCT/US2019/063091.
Non-Final Office Action dated Feb. 19, 2021 for U.S. Appl. No. 17/137,228.
Notice of Allowance dated Apr. 16, 2021 for U.S. Appl. No. 17/137,228.
Supplementary European Search Report dated Aug. 12, 2021 for European Appl. No. 19890096.1.
Examination Report dated Aug. 24, 2021 for European Appl. No. 19890096.1.

* cited by examiner

Fig 1A Amino acid sequence of HB-10716 VH

QVQLQQPGAELVKPGASVKMSCKASGYTFTSYNMHWVKQTPGQGL
                                CDR1

EWIGVIYSGNGDTSYNQKFKGKATLTADKSSSTAYMQINSLTSEDSAVY
      CDR2

YCARERDTRFGNWGQGTLVTVSA
   CDR3

Fig. 1B Amino acid sequence of HB-10716 VL

CDR1
NIVLTQSPASLAVSLGLRATISCRASESVDIYGNSFMHWYQQKPGQPPK

CDR2
LLIYLASNLESGVPARFSGSGSRTDFTLTIDPVEADDAATYYCQQNNEDP

CDR3

YTFGGGTKLEIK

Fig. 2A VH sequence alignment of humanized anti-c-Kit antibodies

```
                    1                   2                     3                    4                     5         a
          1234567890 1234567890 1234567890 1234567890 1234567890 1234567890 123456789
HB-10716  QVQLQQPGAEL VKPGASVKMS CKASGYTFTS YNMHWVKQTP GQGLEWIGVI YSGNGDTSY
AH1       QVQLVQSGAEV KKPGASVKVS CKASGYTFTS YNMHWVRQAP GQGLEWMGVI YSGNGDTSY
AH2       QVQLVQSGAEV KKPGASVKVS CKASGYTFTS YNMHWVRQAP GQGLEWMGVI YSGQGDTSY
AH3       QVQLVQSGAEV KKPGASVKVS CKASGYTFTS YNMHWVRQAP GQGLEWMGVI YSGNGDTSY
AH4       QVQLVQSGAEV KKPGASVKVS CKASGYTFTS YNMHWVRQAP GQGLEWMGVI YSGNGDTSY
AH5       QVQLVQSGAEV KKPGASVKVS CKASGYTFTS YNMHWVRQAP GQGLEWMGVI YSGNGDTSY
AMG191    QVQLVQSGAEV KKPGASVKVS CKASGYTFTS YNMHWVRQAP GQGLEWMGVI YSGNGDTSY
IGHV1-46*01 QVQLVQSGAEV KKPGASVKVS CKASGYTFTS YYMHWVRQAP GQGLEWMGII NPSGGSTSY 6              7              8   abc          9                    10                 11
          0123456789 0123456789 0123456789 0122223456 7890123456 7890123456 78901 234567890 123
HB-10716  NQKFKGKATLT ADKSSSTAYM QINSLTSEDS AVYYCARERD TRFGNWGQGT LVTVSA
AH1       NQKFKGRVTIT ADKSTSTAYM ELSSLRSEDT AVYYCARERD TRFGNWGQGT LVTVSS
AH2       AQKFKGRVTIT ADKSTSTAYM ELSSLRSEDT AVYYCARERD TRFGNWGQGT LVTVSS
AH3       NQKFQGRVTIT ADKSTSTAYM ELSSLRSEDT AVYYCARERD TRFGNWGQGT LVTVSS
AH4       AQKFQGRVTIT ADKSTSTAYM ELSSLRSEDT AVYYCARERD TRFGNWGQGT LVTVSS
AH5       NQKFKGRVTIT ADKSTSTAYM ELSSLRSEDT AVYYCARDRD TRFGNWGQGT LVTVSS
AMG191    NQKFKGRVTIT ADKSTSTAYM ELSSLRSEDT AVYYCARERD TRFGNWGQGT LVTVSS
IGHV1-46*01 AQKFQGRVTMT RDTSTSTVYM ELSSLRSEDT AVYYCAR
```

Fig. 2B VL sequence alignment of humanized anti-ckit antibodies

```
                    1          2       abcd    3              4                5
           12345678901234567890123456777789012345 67890123456789012345 67890123456
HB-10716   NIVLTQSPASLAVSLGLRATISCRASESVDIYGNSFMH--WYQQKPGQPPKLLIYLASNLES
AL1        DIVMTQSPDSLAVSLGERATINCRASDSVDIYGNSFMH--WYQQKPGQPPKLLIYLASNLES
AL2        DIVMTQSPDSLAVSLGERATINCRASESVDIYGQSFMH--WYQQKPGQPPKLLIYLASNLES
AMG191     DIVMTQSPDSLAVSLGERATINCRASESVDIYGNSFMH--WYQQKPGQPPKLLIYLASNLES
IGKV4-1*01 DIVMTQSPDSLAVSLGERATINCKSSQSVLYSSNNKNYLAWYQQKPGQPPKLLIYWASTRES 6         7         8         9         10
           789012345678901234567890123456789012345678901234567
HB-10716   GVPARFSGSGSRTDFTLTIDPVEADDAATYYCQQNNEDPYTFGGGTKLEIK
AL1        GVPDRFSGSGSGTDFTLTISSLQAEDVAVYYCQQNNEDPYTFGGGTKVEIK
AL2        GVPDRFSGSGSGTDFTLTISSLQAEDVAVYYCQQNNEDPYTFGGGTKVEIK
AMG191     GVPDRFSGSGSGTDFTLTISSLQAEDVAVYYCQQNNEDPYTFGGGTKVEIK
IGKV4-1*01 GVPDRFSGSGSGTDFTLTISSLQAEDVAVYYCQQYYSTP
```

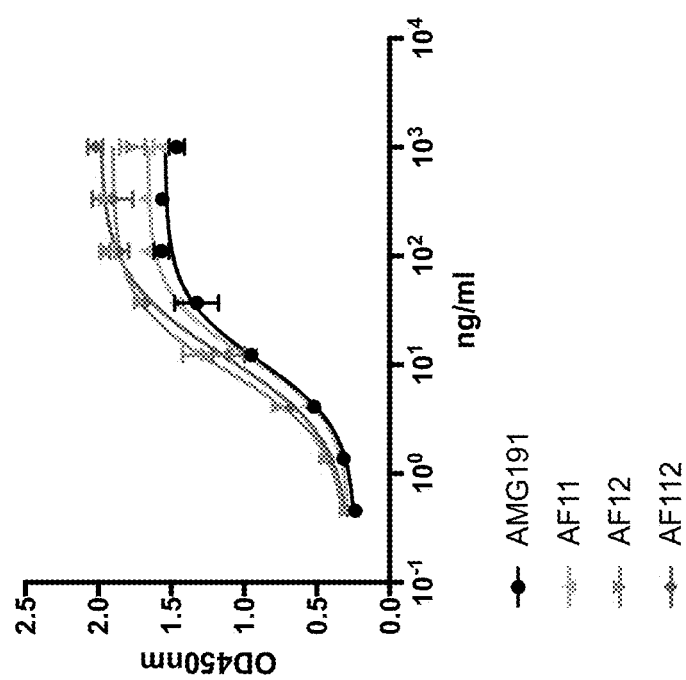
Fig. 2C ELISA Binding

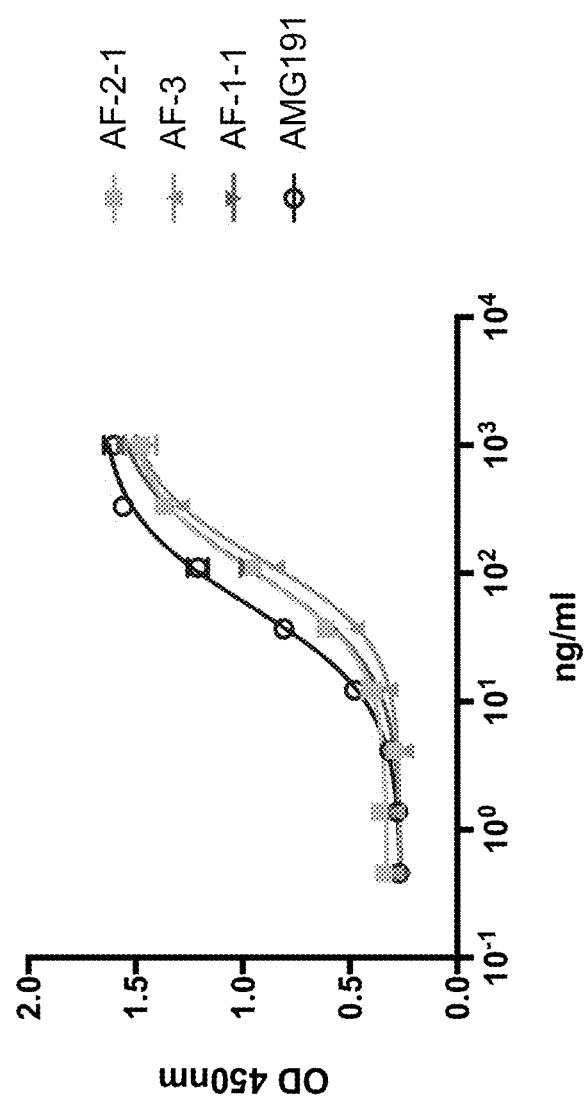
Fig. 2D ELISA Binding

Fig. 3A VH sequence alignment of humanized anti-c-Kit antibodies

```
                        1                   2                   3                   4                   5         a
          1 2 3 4 5 6 7 8 9 0 1 2 3 4 5 6 7 8 9 0 1 2 3 4 5 6 7 8 9 0 1 2 3 4 5 6 7 8 9 0 1 2 3 4 5 6 7 8 9 0 1 2 3 4 5 6 7 8 9
HB-10716  QVQ LQQ PGAEL VK PGASV KMS CKASGYT FTS YNMHW VK QTPGQ LEWI GVI YSGNGDTSY
NH        EVQ LLE SGGGL VQ PGGSL RLS CAAASGFT FTS YNMHW VR QAPGK GLEW VGVI YSGNGDTSY
NH1       EVQ LLE SGGGL VQ PGGSL RLS CAAASGFT FTS YNMHW VR QAPGK GLEW VGVI YSGQGDTSY
NH2       EVQ LLE SGGGL VQ PGGSL RLS CAAASGFT FTS YNMHW VR QAPGK GLEW VGVI YSGNGDTSY
NH3       EVQ LLE SGGGL VQ PGGSL RLS CAAASGFT FTS YNMHW VR QAPGK GLEW VGVI YSGNGDTSY
NH4       EVQ LLE SGGGL VQ PGGSL RLS CAAASGFT FTS YNMHW VR QAPGK GLEW VGVI YSGNGDTSY
NH5       EVQ LLE SGGGL VQ PGGSL RLS CAAASGFT FTS YNMHW VR QAPGQ GLEW MGVI YSGNGDTSY
AMG191    QVQ LVQ SGAEV KK PGASV KVS CKASGYT FTS YAMSW VR QAPGK GLEW MGVI YSGNGDTSY
IGHV3-23*01 EVQ LLE SGGGL VQ PGGSL RLS CAAASGFT FSS YAMSW VR QAPGK GLEW VSAI SGSGSTYY 6                   7                   8     abc         9                   10                  11
          0 1 2 3 4 5 6 7 8 9 0 1 2 3 4 5 6 7 8 9 0 1 2 2 2 2 3 4 5 6 7 8 9 0 1 2 3 4 5 6 7 8 9 0 1 2 3 4 5 6 7 8 9 0 1 2 3
HB-10716  NQK FKGKA TLT ADKSS STAYMQI NSL TSEDSAV YYCAR ERDTR FGN WGQGT LVTVSA
NH        NQK FKGRF TIS ADKSKNT AYL QMNSL RAEDTAV YYCAR ERDTR FGN WGQGT LVTVSS
NH1       NQK FKGRF TIS ADKSKNT AYL QMNSL RAEDTAV YYCAR ERDTR FGN WGQGT LVTVSS
NH2       AQK FKGRF TIS ADKSKNT AYL QMNSL RAEDTAV YYCAR ERDTR FGN WGQGT LVTVSS
NH3       NQK FQGRF TIS ADKSKNT AYL QMNSL RAEDTAV YYCAR ERDTR FGN WGQGT LVTVSS
NH4       AQK FQGRF TIS ADKSKNT AYL QMNSL RAEDTAV YYCAR ERDTR FGN WGQGT LVTVSS
NH5       NQK FKGRF TIS ADKSKNT AYL QMNSL RAEDTAV YYCAR DRDTR FGN WGQGT LVTVSS
AMG191    NQK FKGRV TIT ADKST STAYMEL SSL RSEDTAV YYCAR ERDTR FGN WGQGT LVTVSS
IGHV3-23*01 ADS VKGRF TIS RDNSKNT LYL QMNSL RAEDTAV YYCAK
```

Fig. 3B VL sequence alignment of humanized anti-ckit antibodies

```
                    1             2         abcd    3              4                5
         1234567890123456789012345678 9012345677777890 1234  567890123456789012345 6
HB-10716 NIVLTQSPASLAVSLGLRATI SCRAS ESVDIYGNSFMH---WYQQKPGQPPKLLIYLASNLES
NL       DIVMTQSPLSLPVTPGEPASI SCRAS ESVDIYGNSFMH---WYLQKPGQSPQLLIYLASNLES
NL1      DIVMTQSPLSLPVTPGEPASI SCRAS DSVDIYGNSFMH---WYLQKPGQSPQLLIYLASNLES
NL2      DIVMTQSPLSLPVTPGEPASI SCRAS ESVDIYGQSFMH---WYLQKPGQSPQLLIYLASNLES
AMG191   DIVMTQSPDSLAVSLGERATI NCRAS ESVDIYGNSFMH---WYQQKPGQPPKLLIYLASNLES
IGKV2-28*01 DIVMTQSPLSLPVTPGEPASI SCRSS QSLLHSNGYNYLD-WYLQKPGQSPQLLIYLGSNRAS 6           7          8             9           10
         7890123456789012345678901234567890123456789012345 67
HB-10716 GVPARFSGSGSGSRTDFTLTIDPVEADDAATYYCQQNNEDPYTFGGGTKLEIK
NL       GVPDRFSGSGSGTDFTLKISRVEAEDVGVYYCQQNNEDPYTFGGGTKVEIK
NL1      GVPDRFSGSGSGTDFTLKISRVEAEDVGVYYCQQNNEDPYTFGGGTKVEIK
NL2      GVPDRFSGSGSGTDFTLKISRVEAEDVGVYYCQQNNEDPYTFGGGTKVEIK
AMG191   GVPDRFSGSGSGTDFTLTISSLQAEDVAVYYCQQNNEDPYTFGGGTKVEIK
IGKV2-28*01 GVPDRFSGSGSGTDFTLKISRVEAEDVGVYYCMQALQTP
```

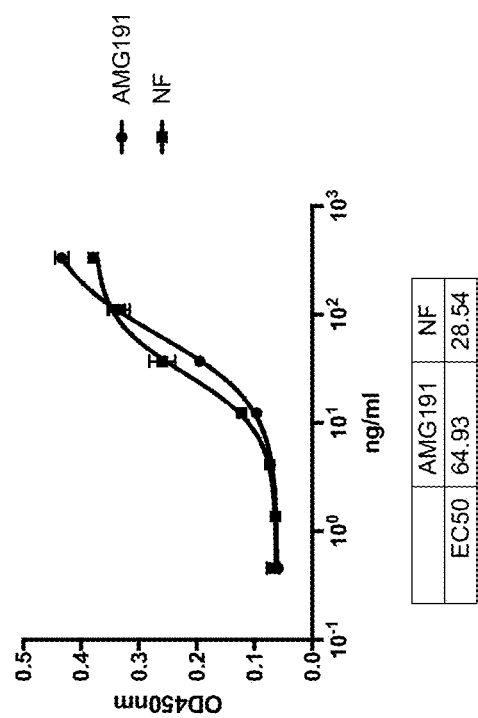

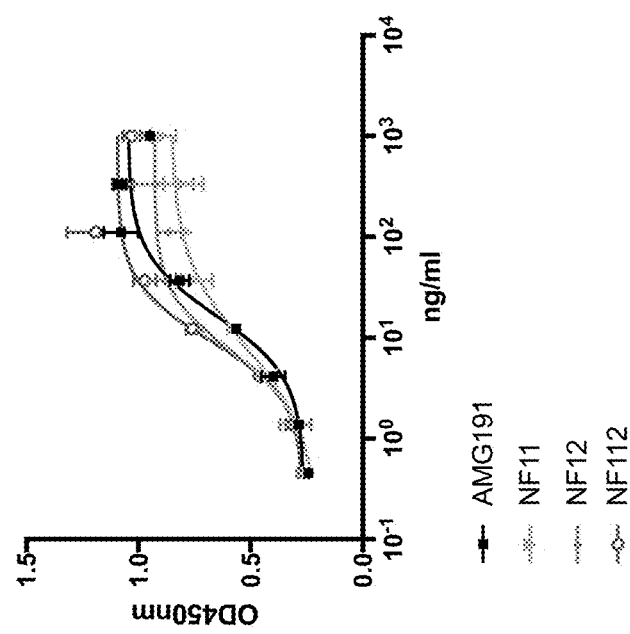
Fig. 3D ELISA binding activity

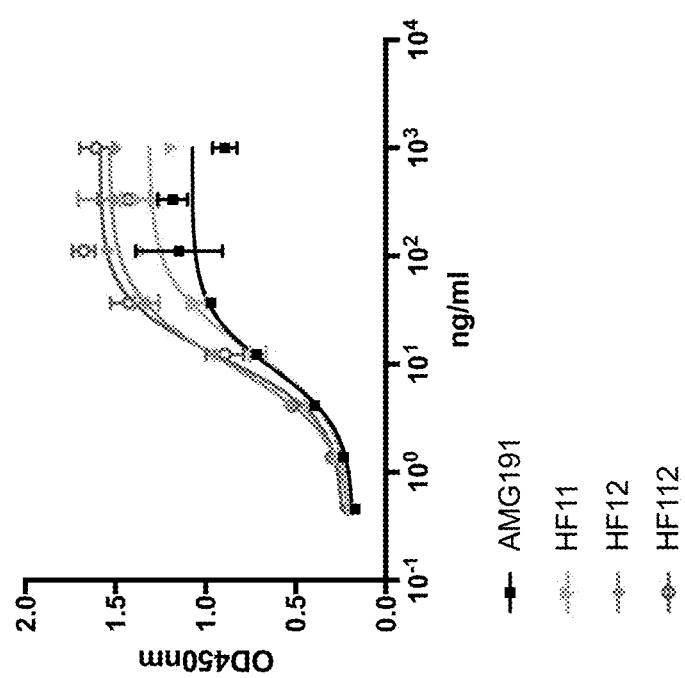

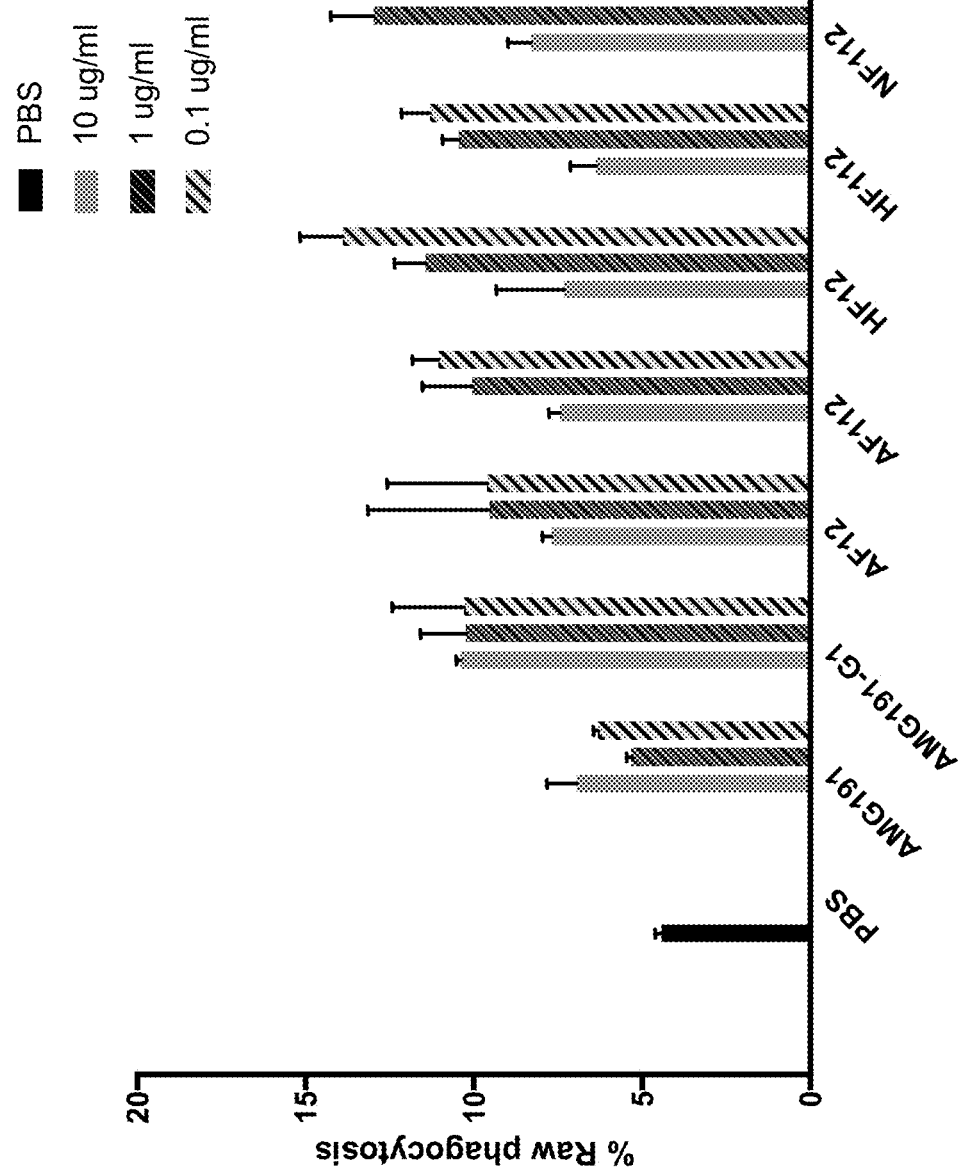
Fig. 5 In vitro Phagocytic Activity

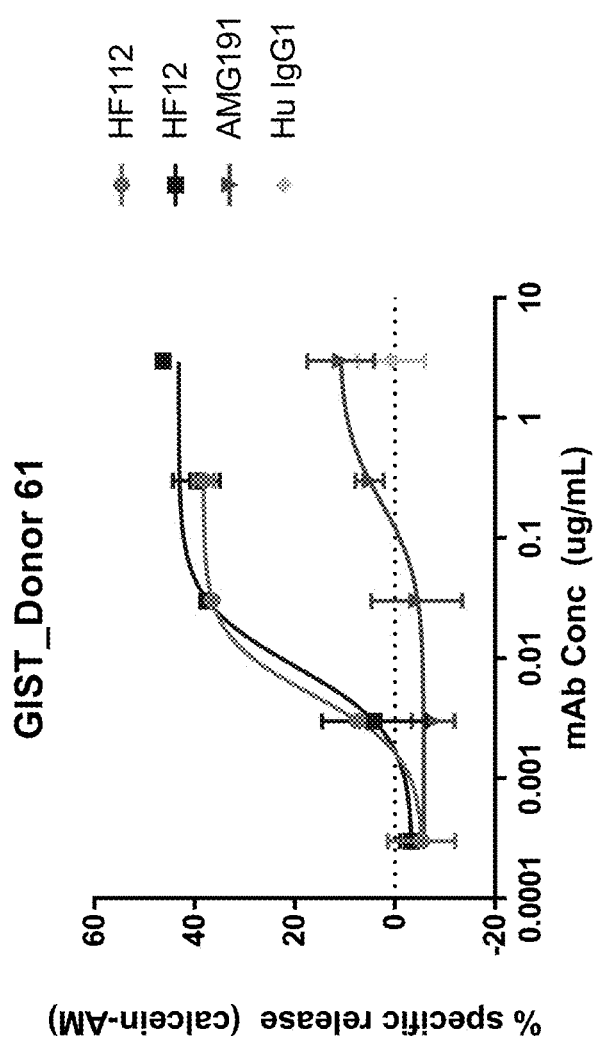
Fig. 6 In vitro ADCC Activity

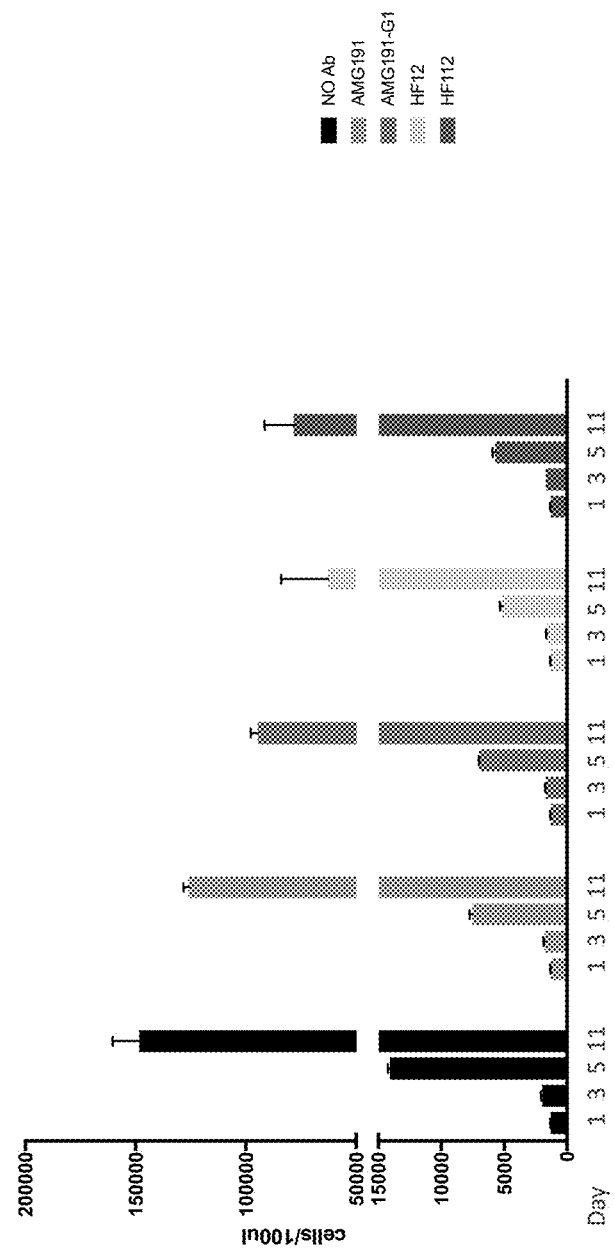

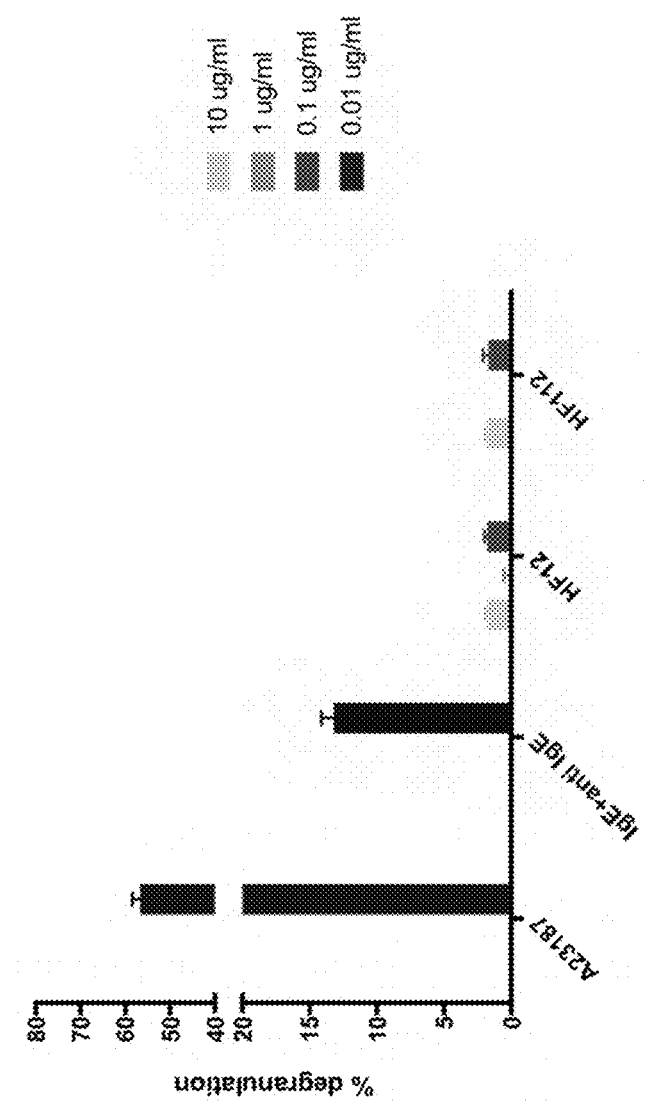

HUMANIZED ANTIBODIES AGAINST C-KIT

CROSS-REFERENCE TO RELATED APPLICATION

The present application claims the benefit of 62/771,526 filed Nov. 26, 2018, which is incorporated by reference in its entirety for all purposes.

REFERENCE TO A SEQUENCE LISTING

The present application includes sequences in txt file 522946SEQLST.TXT, of 31,466 bytes, created Nov. 25, 2019, which is incorporated by reference.

BACKGROUND c-Kit (CD117) is a receptor tyrosine kinase type III, which binds to stem cell factor (SCF), a substance that causes certain types of cells to grow, also known as "steel factor" or "c-Kit ligand." When this receptor binds to stem cell factor, it forms a dimer that activates its intrinsic tyrosine kinase activity, which in turn phosphorylates and activates signal transduction molecules that propagate the signal in the cell. C-Kit is a cell surface marker used to identify certain types of HSPCs in the bone marrow. Hematopoietic stem cells (HSC), multipotent progenitors (MPP), and common myeloid progenitors (CMP) express high levels of c-Kit. It has been proposed that antibodies against c-Kit can be used to ablate endogenous cells in stem cell replacement therapy (WO2016033201, WO2008067115).

SUMMARY OF THE CLAIMED INVENTION

The invention provides an antibody specifically binding to human c-Kit comprising a mature heavy variable region comprising CDRs H1, H2 and H3 as defined by Kabat of SEQ ID NOS:2-4 respectively, and a mature light chain variable region comprising CDRs L1, L2 and L3 as defined by Kabat of SEQ ID NOS:6-8 respectively except that 1, 2, or 3 CDR residue substitutions is/are present selected from N to A at heavy chain position 60, K to Q at heavy chain position 64 and N to Q at light chain position 30, positions being numbered according to Kabat.

Optionally, CDRs H1, H2 and H3 as defined by Kabat are SEQ ID NOS:2-4 respectively, and CDRs L1, L2 and L3 as defined by Kabat are SEQ ID NOS:6-8 respectively except that the substitutions of K to Q at heavy chain position 64 and N to Q at light chain position 30 are present.

Optionally, CDRs H1, H2 and H3 as defined by Kabat are SEQ ID NOS:2-4 respectively, and CDRs L1, L2 and L3 as defined by Kabat are SEQ ID NOS:6-8 respectively except that the substitutions of N to A at heavy chain position 60, K to Q at heavy chain position 64 and N to Q at light chain position 30 are present.

Optionally, the mature heavy chain variable region shows at least 85, 90, 95, 98, or 99%% sequence identity to SEQ ID NO:13, 17 or 21 (AH2, AH3 or AH4) and the mature light chain variable region shows at least 85, 90, 95, 98, 99% sequence identity to SEQ ID NO:53 (NL2) provided any variation from the indicated SEQ ID NOS. is outside the CDRs.

Optionally, heavy chain position 1 by Kabat numbering is E. Optionally, the following positions of the mature light chain variable region are occupied by amino acids as follows: Position 9 occupied by L, Position 12 occupied by P, Position 14 occupied by T, Position 15 occupied by P, Position 18 occupied by P, Position 20 occupied by S, Position 22 occupied by S, Position 37 occupied by L, Position 43 occupied by S, Position 45 occupied by Q Position 74 occupied by K, Position 77 occupied by R, Position 78 occupied by V, Position 79 occupied by E, Position 84 occupied by G. Optionally, the mature heavy chain variable region has a sequence selected from SEQ ID NO: 13, 17 or 21 except that position 1 can be E, and the mature light chain variable region has a sequence of SEQ ID NO:53. Optionally, the mature heavy chain variable region is linked to a heavy chain constant region and the mature light chain variable region is linked to a mature light chain constant region. Optionally, the heavy chain constant region is human IgG1. Optionally, the antibody has enhanced binding to human c-Kit relative to AMG191. Optionally, the antibody has enhanced ADCP relative to AMG191-IgG1. Optionally, the antibody has enhanced ADCC relative to AMG191-IgG1.

The invention further provides a pharmaceutical composition comprising an antibody as described above and a pharmaceutically acceptable carrier.

The invention further provides a method of ablating endogenous HSPCs comprising administering an effective regime of an antibody as described above to a subject in need of ablation.

The invention further provides a method of treating a cancer expressing c-Kit comprising administering an effective regime of an antibody to a subject having the cancer.

Definitions

Monoclonal antibodies or other biological entities are typically provided in isolated form. This means that an antibody or other biologically entity is typically at least 50% w/w pure of interfering proteins and other contaminants arising from its production or purification but does not exclude the possibility that the monoclonal antibody is combined with an excess of pharmaceutically acceptable carrier(s) or other vehicle intended to facilitate its use. Sometimes monoclonal antibodies are at least 60%, 70%, 80%, 90%, 95% or 99% w/w pure of interfering proteins and contaminants from production or purification. Often an isolated monoclonal antibody or other biological entity is the predominant macromolecular species remaining after its purification.

Specific binding is detectably higher in magnitude and distinguishable from nonspecific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that an antibody binds one and only one target. Antibodies of the invention typically specifically bind to c-Kit with an affinity of at least $10^8$, $10^9$, $10^{10}$, $10^{11}$ or $10^{12}$ $M^{-1}$.

The basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region means a light chain variable region without the light chain signal peptide. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. See generally, Fundamental Immunology, Paul, W., ed., 2nd ed. Raven Press, N.Y., 1989, Ch. 7 (incorporated by reference in its entirety for all purposes).

An immunoglobulin light or heavy chain variable region (also referred to herein as a "light chain variable domain" ("VL domain") or "heavy chain variable domain" ("VH domain"), respectively) consists of a "framework" region interrupted by three "complementarity determining regions" or "CDRs." The framework regions serve to align the CDRs for specific binding to an epitope of an antigen. The CDRs include the amino acid residues of an antibody that are primarily responsible for antigen binding. From amino-terminus to carboxyl-terminus, both VL and VH domains comprise the following framework (FR) and CDR regions: FR1, CDR1, FR2, CDR2, FR3, CDR3, and FR4. CDRs 1, 2, and 3 of a VL domain are also referred to herein, respectively, as CDR-L1, CDR-L2, and CDR-L3; CDRs 1, 2, and 3 of a VH domain are also referred to herein, respectively, as CDR-H1, CDR-H2, and CDR-H3.

The assignment of amino acids to each VL and VH domain is in accordance with any conventional definition of CDRs. Conventional definitions include, the Kabat definition (Kabat, Sequences of Proteins of Immunological Interest (National Institutes of Health, Bethesda, Md., 1987 and 1991), the Chothia definition (Chothia & Lesk, J. Mol. Biol. 196:901-917, 1987; Chothia et al., Nature 342:878-883, 1989); a composite of Chothia Kabat CDR in which CDR-H1 is a composite of Chothia and Kabat CDRs; the AbM definition used by Oxford Molecular's antibody modelling software; and, the contact definition of Martin et al. (world wide web bioinfo.org.uk/abs). Kabat provides a widely used numbering convention (Kabat numbering) in which corresponding residues between different heavy chains or between different light chains are assigned the same number. Unless otherwise specified numbering of positions within the variable regions of antibodies is Kabat numbering. When an antibody is said to comprise CDRs by a certain definition of CDRs (e.g., Kabat) that definition specifies the minimum number of CDR residues present in the antibody (i.e., the Kabat CDRs). It does not exclude that other residues falling within another conventional CDR definition but outside the specified definition are also present. For example, an antibody comprising CDRs defined by Kabat includes among other possibilities, an antibody in which the CDRs contain Kabat CDR residues and no other CDR residues, and an antibody in which CDR H1 is a composite Chothia-Kabat CDR H1 and other CDRs contain Kabat CDR residues and no additional CDR residues based on other definitions.

The term "antibody" includes intact antibodies and binding fragments thereof. Typically, fragments compete with the intact antibody from which they were derived for specific binding to the target including separate heavy chains, light chains Fab, Fab', F(ab')2, F(ab)c, Dabs, nanobodies, and Fv. Fragments can be produced by recombinant DNA techniques, or by enzymatic or chemical separation of intact immunoglobulins. The term "antibody" also includes a bispecific antibody and/or a humanized antibody. A bispecific or bifunctional antibody is an artificial hybrid antibody having two different heavy/light chain pairs and two different binding sites (see, e.g., Songsivilai and Lachmann, Clin. Exp. Immunol., 79:315-321 (1990); Kostelny et al., J. Immunol., 148:1547-53 (1992)).

Exemplary bispecific antibodies can also be: (1) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (2) a Tandab, which is a fusion of two single chain diabodies resulting in a tetravalent bispecific antibody that has two binding sites for each of the target antigens; (3) a flexibody, which is a combination of scFvs with a diabody resulting in a multivalent molecule; (4) a so-called "dock and lock" molecule, based on the "dimerization and docking domain" in Protein Kinase A, which, when applied to Fabs, can yield a trivalent bispecific binding protein consisting of two identical Fab fragments linked to a different Fab fragment; or (5) a so-called Scorpion molecule, comprising, e.g., two scFvs fused to both termini of a human Fc-region. Examples of platforms useful for preparing bispecific antibodies include BiTE (Micromet), DART (MacroGenics), Fcab and Mab2 (F-star), Fc-engineered IgGI (Xencor) or DuoBody (based on Fab arm exchange, Genmab).

The term "epitope" refers to a site on an antigen to which an antibody binds. An epitope can be formed from contiguous amino acids or noncontiguous amino acids juxtaposed by tertiary folding of one or more proteins. Epitopes formed from contiguous amino acids (also known as linear epitopes) are typically retained on exposure to denaturing solvents whereas epitopes formed by tertiary folding (also known as conformational epitopes) are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996).

Competition between antibodies is determined by an assay in which an antibody under test inhibits specific binding of a reference antibody to a common antigen (see, e.g., Junghans et al., Cancer Res. 50:1495, 1990). A test antibody competes with a reference antibody if an excess of a test antibody (e.g., at least 2×, 5×, 10×, 20× or 100×) inhibits binding of the reference antibody by at least 50% as measured in a competitive binding assay. Some test antibodies inhibit binding of the references antibody by at least 75%, 90% or 99%. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

The term "pharmaceutically acceptable" means that the carrier, diluent, excipient, or auxiliary is compatible with the other ingredients of the formulation and not substantially deleterious to the recipient thereof and/or that such carrier diluent, excipient or auxiliary is approved or approvable by the FDA for inclusion in a pharmaceutical composition for parenteral administration to humans.

The term "subject" includes human and other mammalian subjects that receive either prophylactic or therapeutic treatment.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Percentage sequence identities are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Compositions or methods "comprising" or "including" one or more recited elements may include other elements not specifically recited. For example, a composition that "comprises" or "includes" an antibody may contain the antibody alone or in combination with other ingredients.

Designation of a range of values includes all integers within or defining the range, and all subranges defined by integers within the range.

Unless otherwise apparent from the context, the term "about" encompasses insubstantial variations, such as values within a standard margin of error of measurement (e.g., SEM) of a stated value.

Statistical significance means p<0.05.

A humanized antibody is a genetically engineered antibody in which CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539; Carter, U.S. Pat. No. 6,407,213; Adair, U.S. Pat. No. 5,859,205; and Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having CDRs entirely or substantially from a donor antibody and variable region framework sequences and constant regions, if present, entirely or substantially from human antibody sequences. A CDR in a humanized antibody is substantially from a corresponding CDR in a non-human antibody when at least 85%, 90%, 95% or 100% of corresponding residues (as defined by Kabat) are identical between the respective CDRs. The variable region framework sequences of an antibody chain or the constant region of an antibody chain are substantially from a human variable region framework sequence or human constant region respectively when at least 85%, 90%, 95% or 100% of corresponding residues defined by Kabat are identical to a human acceptor sequence.

BRIEF DESCRIPTION OF THE FIGURES

FIGS. 1A and 1B show the mature heavy and light chain variable regions of the mouse anti-c-Kit antibody produced by a hybridoma deposited as HB-10716.

FIGS. 2A and 2B show mature heavy and light chain variable regions of five humanized heavy chain mature variable regions of the present invention and two humanized light chain mature variable regions compared with mouse and human acceptor sequences. The variable region frameworks of the humanized sequences are the same as those of AMG191 but the CDRs are different.

FIG. 2C compares binding of AMG191 with variants thereof having CDR substitutions. All of the CDR substituted variants showed enhanced binding.

FIG. 2D compares binding of AMG191 with variants having other CDRs substitutions. These variants showed reduced binding.

FIGS. 3A and 3B provide the sequence of six humanized heavy chain mature variable regions and three humanized light chain mature variable regions compared with AMG191, mouse sequences and human acceptor sequences. In these humanized chains, the variable region frameworks differ from those in the AMG191 antibody. Some of the humanized chain also differ in the CDRs.

FIG. 3C compares binding of AMG191 to a humanized antibody with the same CDRs but different variable region frameworks (arising from use of different human acceptor sequences). The antibody with the new frameworks (NF) has higher affinity.

FIG. 3D compares binding of AMG191 to additional humanized variants based on the new frameworks and also having CDR substitutions relative to AMG191. All three of the variant antibodies had higher affinity.

FIG. 4 compares binding of AMG191 to three humanized antibodies differing from AMG191 by the presence of CDR substitutions and a different light chain variable region framework (the heavy chain variable region framework being the same). All three of the variant antibodies had higher affinity.

FIG. 5 compares phagocytic activity of AMG191, a variant of AMG191 having a wildtype IgG1 constant region with, five new humanized antibodies of the present invention. The new variants particularly HF12 and NF112 showed increased phagocytosis particularly at the lower concentrations tested.

FIG. 6 compares ADCC activity of AMG191 with two new humanized variants HF112 and HF12 and an isotype matched irrelevant control. HF112 and HF12 had more ADCC activity.

FIG. 7 shows inhibition of SCF-induced HSPC proliferation by HF12 and HF112 compared with AMG191, AMG191-human IgG1 and a negative control.

FIG. 8 compares mast cell degranulation of anti-c-Kit antibodies compared with positive controls A23187 and IgE+anti-IgE.

BRIEF DESCRIPTION OF SEQUENCES

SEQ ID NOS:1-4 are the mature heavy variable region and CDRs-H1, H2 and H3 of the antibody of HB-10716.

SEQ ID NOS:5-8 are the mature light chain variable region and CDRs-L1, L2 and L3 of the antibody of HB-10716.

SEQ ID NOS:9-12 are the mature heavy chain variable region and CDRs-H1, H2 and H3 of the humanized heavy chain AH1.

SEQ ID NOS:13-16 are the mature heavy chain variable region and CDRs-H1, H2 and H3 of the humanized heavy chain AH2.

SEQ ID NOS:17-20 are the mature heavy chain variable region and CDRs-H1, H2 and H3 of the humanized heavy chain AH3.

SEQ ID NOS:21-24 are the mature heavy chain variable region and CDRs-H1, H2 and H3 of the humanized heavy chain AH4.

SEQ ID NOS:25-28 are the mature heavy chain variable region and CDRs-H1, H2 and H3 of the humanized heavy chain AH5.

SEQ ID NO:29 is the mature heavy chain variable region of AMG191.

SEQ ID NO:30 is a variable region sequence of IGHV1-46*01.

SEQ ID NOS:31-34 are the mature light chain variable region and CDRs-L1, L2 and L3 of the humanized light chain variable region AL1.

SEQ ID NOS:35-38 are the mature light chain variable region and CDRs-L1, L2 and L3 of the humanized light chain AL2.

SEQ ID NO:39 is the mature light chain variable region of AMG191.

SEQ ID NOS:40-43 are the variable region sequence and three CDRs-L1, L2 and L3, of IGKV4-1*01.

SEQ ID NOS:44-50 are the mature heavy chain variable region of humanized heavy chains NH, NH1, NH2, NH3, NH4 and NH5 and IGHV3-23*01.

SEQ ID NOS:51-54 are the mature light chain variable regions of humanized light chains NL, NL1, NL2, and IGKV2-28*01.

DETAILED DESCRIPTION

I. General

The invention provides antibodies specifically binding to human c-Kit (Swiss Prot P10721). The antibodies represent humanized forms of the previously disclosed mouse anti-c-Kit antibody produced by the hybridoma deposited as HB-10716, which has mature heavy and light chain variable regions of SEQ ID NOS:1 and 5 respectively. This mouse antibody has previously been humanized as AMG191 (see U.S. Pat. No. 7,915,391). The Kabat CDRs of AMG191 are the same as the mouse antibody from which it was derived. AMG191 is commercially available from Creative Biolabs.

The present antibodies have CDRs substantially from the mouse antibody deposited as HB-10716 engrafted into human acceptor sequences, optionally with substitutions at certain positions as further described below.

Some antibodies comprise a mature heavy variable region comprising CDRs H1, H2 and H3 of SEQ ID NO:1, and a mature light chain variable region comprising CDRs L1, L2 and L3 of SEQ ID NO:5 provided that at least one CDR residue substitution is present. CDRs H1, H2 and H3 preferably comprise SEQ ID NOS:2-4 respectively and CDRs L1, L2 and L3 preferably comprise SEQ ID NOS:6-8 (i.e., as defined by Kabat) provided that at least one CDR substitution is present. The CDR substitution is preferably selected from N to A at heavy chain position 60, K to Q at heavy chain position 64 and N to Q at light chain position 30, positions being numbered according to Kabat. One, two or all three of these substitutions can be present. Some antibodies include the substitutions at heavy chain position 64 and light chain position 30. Some antibodies include the substitutions at heavy chain position 60, heavy chain position 64 and light chain position 30. Some antibodies include the substitutions at heavy chain position 60 and light chain position 30. Some antibodies included the substitutions at heavy chain position 60 and heavy chain position 64. Some antibodies have no substitutions of the Kabat CDRs except the substitutions at heavy chain positions 60 and 64 and light chain position 30 individually or in the listed combinations. If any other substitutions of the Kabat CDRs are present, it is preferred no more than 1, 2, 3, 4 or 5, such other substitutions are present.

Some of the present antibodies differ from AMG191 by the presence of at least one substitution of a CDR residue relative to the residue present at AMG191. Preferred substitutions are N to A at heavy chain position 60, K to Q at heavy chain position 64 and N to Q at a light chain position 30, positions being numbered according to Kabat. One, two or all three of these substitutions can be present. Some antibodies include the substitutions at heavy chain position 64 and light chain position 30. Some antibodies include the substitutions at heavy chain position 60, heavy chain position 64 and light chain position 30. Some antibodies include the substitutions at heavy chain position 60 and light chain position 30. Some antibodies included the substitutions at heavy chain position 60 and heavy chain position 64. Some antibodies have no substitutions relative to the Kabat CDRs of AMG191 except the substitutions at heavy chain positions 60 and 64 and light chain position 30 individually or in the listed combinations. If any other substitutions of the Kabat CDRs are present, it is preferred no more than 1, 2, 3, 4 or 5, such other substitutions are present The CDRs substitutions at heavy chain positions 60 and 64 and light chain position 30 individually and in combination can confer increased binding affinity for human c-Kit. The substitutions also represent replacement of a mouse residue with a human germline residue for a position thus other things being equal increasing the human character of the humanized antibody. Table 1 below compares the residues occupying heavy chain positions 60 and 64 and light chain position 30 in the mouse antibody deposited as HB-10716, AMG191 and three of the present humanized antibodies:

TABLE 1

| Residue | HB-10716 | AMG191 | HF12 | HF11 | HF112 |
|---------|----------|--------|------|------|-------|
| H60 | N | N | A | N | A |
| H64 | K | K | K | Q | Q |
| L30 | N | N | Q | Q | Q |

Additionally or alternatively, some of the present humanized antibodies differ from those of AMG191 by the presence of different variable region framework sequences. AMG191 was derived by grafting mouse CDR sequences into the germline frameworks of IGHV1-46*01 IGKV4-1*01 for the heavy and light chains respectively. The present disclosure provides for grafting CDRs into a heavy chain variable region framework of IGH3-23*01 and a light chain variable region framework of IGKV2-28*01. It has been found that these frameworks confer a higher binding affinity than those of AMG191. Some preferred antibodies of the invention include a heavy chain variable region framework based on IGHV1-46*01 incorporating the same back mutations as in the heavy chain variable region of AMG191 and a light chain variable region framework based on IGKV2-28*01. Such a combination of frameworks combines advantages of improved affinity relative to AMG191 with improved expression over antibodies with a combination of a heavy chain variable region framework of IGH3-23*01 and a light chain variable region framework of IGKV2-28*01.

Thus, some preferred antibodies of the invention have a mature heavy chain variable region having a sequence of any of the chains designated SEQ ID NOS:13, 17 or 21 corresponding to AH2, AH3, and AH4 and a mature light chain variable region having a sequence of SEQ ID NO:53 corresponding to NL2. The heavy chain variable region sequences differ from one another by having CDR substitutions at heavy chain position 60 only, heavy chains position 64 only, or heavy chain positions 60 and 64, all by Kabat numbering. Other than the CDR substitutions, the heavy chain variable region sequences are the same as the mature heavy chain variable region of AMG191. The heavy chain sequences of SEQ ID NOS:13, 17 and 21 include variable region framework substitutions (i.e., human acceptor residue to mouse donor) at Kabat positions 71 (R to A), 73 (T to K) and 78 (V to A). There is an additional substitution at position 69 of M to I.

The mature light chain variable region of SEQ ID NO:53 has a CDR substitution at position 30. The mature light chain variable region of SEQ ID NO:53 also differs from the mature light chain variable region of AMG191 in several positions in the variable region framework as follows due to the different acceptor selections:

Position 9 occupied by L
Position 12 occupied by P
Position 14 occupied by T
Position 15 occupied by P
Position 18 occupied by P
Position 20 occupied by S
Position 22 occupied by S
Position 37 occupied by L
Position 43 occupied by S
Position 45 occupied by Q
Position 74 occupied by K
Position 77 occupied by R
Position 78 occupied by V
Position 79 occupied by E
Position 84 occupied by G.

The mature light chain variable region of SEQ ID NO:53 does not contain any back mutations of the variable region framework to mouse residues from human germline.

The invention also provides antibodies having heavy and light chain variable regions representing variants of exemplified sequences. For example, the invention includes antibodies having a mature heavy chain variable region having at least 85%, 90%, 95%, 98 or 99% identity to any of SEQ ID NOS:13, 17 or 21 and a mature light chain variable region having at least 85%, 90%, 95%, 98% or 99% sequence identity to SEQ ID NO:53. Any variation from the designated sequences is preferably outside the CDRs as defined by Kabat. Variation is also preferably not at variable region framework positions subject of back mutations in the indicated sequences (positions 71, 73 and 78 by Kabat numbering). In some antibodies, any substitution is not at heavy chain position 69 by Kabat numbering. In some antibodies, variation is at variable region framework position(s) other than those at which SEQ ID NO:53 differs from the mature light chain variable region of AMG191. In other antibodies, variation is at variable region framework position(s) at which SEQ ID NO:53 differs from the mature light chain variable region of AMG191, optionally in combination with other position(s) in the variable region frameworks. In some antibodies, at least 1, 2, 3, 4, 5, 6, 7, 8, 9, 10, 11, 12, 13, 14, or 15 of the variable region framework residues at which SEQ ID NO:53 differs from the mature light chain variable region framework of AMG191 is retained. In some antibodies, variation is by way of conservative substitution(s). In some antibodies, the Q at position 1 of the heavy chain can be replaced by an E reducing potential for pyroglutamate conversion (Liu, et al., 2011, J. Biol. Chem., 286: 11211-11217). Glutamic acid (E) conversion to pyroglutamate (pE) occurs more slowly than from glutamine (Q). Because of the loss of a primary amine in the glutamine to pE conversion, antibodies become more acidic. Incomplete conversion produces heterogeneity in the antibody that can be observed as multiple peaks using charge-based analytical methods. Heterogeneity differences may indicate a lack of process control.

Antibodies can be tested for binding affinity to human c-Kit, ADCP, ADCC and inhibition of SCF-induced HSPC proliferation using the assays provided in the examples. Antibodies can also be screened in animal models, such as described in WO2016033201. Preferred antibodies of the invention have enhanced binding affinity to human c-Kit, enhanced ADCP and/or enhanced ADCC and/or enhanced inhibition of SCF-induced HSPC proliferation measured using such assays over AMG191 or a human IgG1 form thereof. Preferred antibodies also inhibit binding of human-c-Kit to its ligand human stem cell factor.

The invention also provides a means for enhanced binding to human c-Kit and/or ADCP and/or ADCC against cells expressing human c-Kit compared with AMG191 or a human IgG1 form thereof, wherein enhancement is measured as in the present Examples. Exemplary means are antibodies having a mature heavy chain variable region of any of SEQ ID NOS:13, 17 or 21 and a mature light chain variable region of SEQ ID NO:53 with a human IgG1 heavy chain constant region and human kappa light chain constant region. Substitutions relative to AMG191 within the CDRs of N to A at heavy chain position 60, K to Q at heavy chain position 64 and/or N to Q at a light chain position 30 contribute to the enhanced properties of the exemplary means. Such means can be incorporated in a pharmaceutical composition with a pharmaceutically active carrier.

Antibodies may or may not be subject to posttranslational modification, such as glycosylation, depending on conditions of expression or selection of constant region among other factors.

II. Selection of Constant Region

The heavy and light chain variable regions described above can be linked to at least a portion of a human constant region. The choice of constant region depends, in part, whether antibody-dependent cell-mediated cytotoxicity, antibody dependent cellular phagocytosis and/or complement dependent cytotoxicity are desired. For example, human isotypes IgG1 and IgG3 have complement-dependent cytotoxicity and human isotypes IgG2 and IgG4 do not. Human IgG1 and IgG3 also induce stronger cell mediated effector functions than human IgG2 and IgG4. Human IgG1 is preferred for the present antibodies. Light chain constant regions can be lambda or kappa.

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC or remove a glycosylation site (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004). Exemplary substitutions include a Gln at position 250 and/or a Leu at position 428 (EU numbering is used in this paragraph for the constant region) for increasing the half-life of an antibody. M252Y/S254T/T256E also increase half-life as does N434A or S, T250Q, and V3089P Substitution at any or all of positions 234, 235, 236 and/or 237 reduce affinity for Fcγ receptors, particularly FcγRI receptor (see, e.g., U.S. Pat. No. 6,624,821). Any of the following substitutions increase effector function: F243L/R292P/Y300L/V305I/P396L, F243L/R292P/Y300L/V305I/P396L, S239D/I332E, S239D/I332E/A330L, S298A/E333A/K334A, S239D/I332E, S239D/I332E/A330L, and S298A/E333A/K334A.

Human constant regions show allotypic variation and isoallotypic variation between different individuals, that is, the constant regions can differ in different individuals at one or more polymorphic positions. Isoallotypes differ from allotypes in that sera recognizing an isoallotype bind to a non-polymorphic region of a one or more other isotypes.

III. Expression of Recombinant Antibodies

Humanized antibodies are typically produced by recombinant expression. Recombinant polynucleotide constructs typically include an expression control sequence operably linked to the coding sequences of antibody chains, including naturally associated or heterologous expression control elements, such as a promoter. The expression control sequences can be promoter systems in vectors capable of transforming or transfecting eukaryotic or prokaryotic host cells. Once the vector has been incorporated into the appropriate host, the host is maintained under conditions suitable for high level expression of the nucleotide sequences and the collection and purification of the crossreacting antibodies.

These expression vectors are typically replicable in the host organisms either as episomes or as an integral part of the host chromosomal DNA. Commonly, expression vectors contain selection markers, e.g., ampicillin resistance or hygromycin resistance, to permit detection of those cells transformed with the desired DNA sequences.

E. coli is one prokaryotic host useful for expressing antibodies, particularly antibody fragments. Microbes, such as yeast, are also useful for expression. Saccharomyces is a yeast host with suitable vectors having expression control sequences, an origin of replication, termination sequences, and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

Mammalian cells can be used for expressing nucleotide segments encoding immunoglobulins or fragments thereof. See Winnacker, From Genes to Clones, (VCH Publishers, N Y, 1987). A number of suitable host cell lines capable of secreting intact heterologous proteins have been developed, and include CHO cell lines, various COS cell lines, HeLa cells, HEK293 cells, L cells, and non-antibody-producing myelomas including Sp2/0 and NS0. The cells can be nonhuman. Expression vectors for these cells can include expression control sequences, such as an origin of replication, a promoter, an enhancer (Queen et al., Immunol. Rev. 89:49 (1986)), and necessary processing information sites, such as ribosome binding sites, RNA splice sites, polyadenylation sites, and transcriptional terminator sequences. Expression control sequences can include promoters derived from endogenous genes, cytomegalovirus, SV40, adenovirus, bovine papillomavirus, and the like. See Co et al., J. Immunol. 148:1149 (1992).

Alternatively, antibody coding sequences can be incorporated in transgenes for introduction into the genome of a transgenic animal and subsequent expression in the milk of the transgenic animal (see, e.g., U.S. Pat. Nos. 5,741,957; 5,304,489; and 5,849,992). Suitable transgenes include coding sequences for light and/or heavy chains operably linked with a promoter and enhancer from a mammary gland specific gene, such as casein or beta lactoglobulin.

The vectors containing the DNA segments of interest can be transferred into the host cell by methods depending on the type of cellular host. For example, calcium chloride transfection is commonly utilized for prokaryotic cells, whereas calcium phosphate treatment, electroporation, lipofection, biolistics, or viral-based transfection can be used for other cellular hosts. Other methods used to transform mammalian cells include the use of polybrene, protoplast fusion, liposomes, electroporation, and microinjection. For production of transgenic animals, transgenes can be microinjected into fertilized oocytes or can be incorporated into the genome of embryonic stem cells, and the nuclei of such cells transferred into enucleated oocytes.

Having introduced vector(s) encoding antibody heavy and light chains into cell culture, cell pools can be screened for growth productivity and product quality in serum-free media. Top-producing cell pools can then be subjected of FACS-based single-cell cloning to generate monoclonal lines. Specific productivities above 50 pg or 100 pg per cell per day, which correspond to product titers of greater than 7.5 g/L culture, can be used. Antibodies produced by single cell clones can also be tested for turbidity, filtration properties, PAGE, IEF, UV scan, HP-SEC, carbohydrate-oligosaccharide mapping, mass spectrometry, and binding assay, such as ELISA or Biacore. A selected clone can then be banked in multiple vials and stored frozen for subsequent use.

Once expressed, antibodies can be purified according to standard procedures of the art, including protein A capture, HPLC purification, column chromatography, gel electrophoresis and the like (see generally, Scopes, Protein Purification (Springer-Verlag, NY, 1982)).

Methodology for commercial production of antibodies can be employed, including codon optimization, selection of promoters, selection of transcription elements, selection of terminators, serum-free single cell cloning, cell banking, use of selection markers for amplification of copy number, CHO terminator, or improvement of protein titers (see, e.g., U.S. Pat. Nos. 5,786,464; 6,114,148; 6,063,598; 7,569,339; WO2004/050884; WO2008/012142; WO2008/012142; WO2005/019442; WO2008/107388; WO2009/027471; and U.S. Pat. No. 5,888,809).

IV. Nucleic Acids

The invention further provides nucleic acids encoding any of the heavy and light chains described above. Optionally, such nucleic acids further encode a signal peptide and can be expressed with the signal peptide linked to the constant region Coding sequences of nucleic acids can be operably linked with regulatory sequences to ensure expression of the coding sequences, such as a promoter, enhancer, ribosome binding site, transcription termination signal, and the like. The nucleic acids encoding heavy and light chains can occur in isolated form or can be cloned into one or more vectors. The nucleic acids can be synthesized by, for example, solid state synthesis or PCR of overlapping oligonucleotides. Nucleic acids encoding heavy and light chains can be joined as one contiguous nucleic acid, e.g., within an expression vector, or can be separate, e.g., each cloned into its own expression vector.

V. Conjugated Antibodies

The antibodies of the present invention can be conjugated to cytotoxic or cytostatic moieties to provide an addition mechanism of cytotoxicity.

Some such antibodies can be modified to act as immunotoxins. See, e.g., U.S. Pat. No. 5,194,594. For example, ricin, a cellular toxin derived from plants, can be coupled to antibodies by using the bifunctional reagents S-acetylmercaptosuccinic anhydride for the antibody and succinimidyl 3-(2-pyridyldithio)propionate for ricin. See Pietersz et al., Cancer Res. 48(16):4469-4476 (1998). The coupling results in loss of B-chain binding activity of ricin, while impairing neither the toxic potential of the A-chain of ricin nor the activity of the antibody. Similarly, saporin, an inhibitor of ribosomal assembly, can be coupled to antibodies via a disulfide bond between chemically inserted sulfhydryl groups. See Polito et al., Leukemia 18:1215-1222 (2004).

Some such antibodies can be linked to radioisotopes. Examples of radioisotopes include, for example, yttrium90 (90Y), indium111 (111In), 131I, 99mTc, radiosilver-111, radiosilver-199, and Bismuth213. Linkage of radioisotopes to antibodies may be performed with conventional bifunctional chelates. For radiosilver-111 and radiosilver-199 linkage, sulfur-based linkers may be used. See Hazra et al., Cell Biophys. 24-25:1-7 (1994). Linkage of silver radioisotopes may involve reducing the immunoglobulin with ascorbic acid. For radioisotopes such as 111In and 90Y, ibritumomab tiuxetan can be used and will react with such isotopes to form 111In-ibritumomab tiuxetan and 90Y-ibritumomab tiuxetan, respectively. See Witzig, Cancer Chemother. Pharmacol., 48 Suppl 1:S91-S95 (2001).

Some such antibodies can conjugated with toxic chemotherapeutic drugs such as maytansine, geldanamycin, tubulin inhibitors such as tubulin binding agents (e.g., auristatins), or minor groove binding agents such as calicheamicin.

VI. Therapeutic Applications

Antibodies of the invention or pharmaceutical compositions incorporating such antibodies can be used for treatment of various conditions. For example, such antibodies can be used in ablation of endogenous hematopoietic stem and progenitor cells (HSPCs) in a subject in need thereof. Ablation of endogenous HSPCs is an initial step in stem cell replacement therapy. Stem cell replacement therapy generally involves reducing or eliminating endogenous HSPCs, which are defective in some respect, and replacing them with replacement HSPCs. The replacement HSPCs can be autologous, allogenic or xenogeneic. Endogenous HSPCs may be defective as a result of hereditary mutation impairing function or expression (e.g., sickle cell anemia or thalassemia), as a result of a hematologic cancer, or as a result of damage from chemotherapy used in treating a cancer. Endogenous HSPCs may also be replaced in conjunction with an organ transplant because the endogenous HSPCs would result in immune attack of the transplant.

Antibodies against c-Kit can also be used in treatment of cancers expressing c-Kit. Such cancers include hematological cancers, such as AML and solid tumors, such as mast cell cancer, testicular stromal cancer, gastrointestinal stromal cancer, melanoma, breast and lung cancer. Expression of c-Kit is preferably at a higher level than tissue matched normal control cells as determined by immunohistochemistry assay.

Antibodies are administered in an effective regime meaning a dosage, route of administration and frequency of administration that achieves the intended purpose, such as reduction of endogenous HSPCs or of cancer cells expressing c-Kit. In some instances, efficacy can be observed in an individual patient relative to historical controls or past experience in the same patient. In other instances, efficacy can be demonstrated in a preclinical or clinical trial in a population of treated patients relative to a control population of untreated patients.

Exemplary dosages are at least 0.05 mg/k and up to 10 mg/kg e.g., about 0.05-10 mg/kg, or 0.1 to 5 mg/kg or 5-750 mg as a fixed dosage. The dosage depends on the condition of the patient and response to prior treatment, if any, whether the treatment is prophylactic or therapeutic and whether the disorder is acute or chronic, among other factors.

Administration can be parenteral, intravenous, oral, subcutaneous, intra-arterial, intracranial, intrathecal, intraperitoneal, topical, intranasal or intramuscular. Some antibodies can be administered into the systemic circulation by intravenous or subcutaneous administration. Intravenous administration can be, for example, by infusion over a period such as 30-90 min.

The antibody can be administered once or multiple times. If multiple times, the intervals can be e.g., daily, weekly, every two weeks, every month or every quarter.

VI. Pharmaceutical Compositions and Methods of Use

Pharmaceutical compositions incorporating an antibody of the invention for parenteral administration can be sterile and substantially isotonic (250-350 mOsm/kg water) and manufactured under GMP conditions. Pharmaceutical compositions can be provided in unit dose form (i.e., the dose for a single administration). Pharmaceutical compositions can be formulated using one or more pharmaceutically acceptable carriers, diluents, excipients or auxiliaries. The formulation depends on the route of administration chosen. For injection, antibodies can be formulated in aqueous solutions, e.g., in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use.

The regimes can be administered in combination with another agent effective in treatment of the condition being treated (e.g., chemotherapy agents or biologics for treatment of cancer).

After treatment, the treated subject's condition can be monitored for changes responsive to treatment (e.g., reduced numbers of endogenous HSPCs) or reduced numbers of cancer cells expressing c-Kit.

VII. Other Uses

The antibodies of the invention can also be used for detecting c-Kit by immuno assay, such as ELISA, Western blot, or immunohistochemistry. Such testing can be useful in determining whether a cancer expresses c-Kit making it amenable to treatment with the present methods. The antibodies can also be used for enriched of HSPCs expressing c-Kit by affinity chromatography.

EXAMPLES

1. Materials and Methods

Antibody V Cloning and Sequencing.

An anti-human c-kit hybridoma cell line was purchased from ATCC (HB-10716). The heavy (VH) and light chain (VL) variable regions were cloned and sequenced by Genscript.

Antibody Humanization and CDR Substitutions.

Humanization of HB-10716 was performed by installing CDR residues from mouse antibodies onto human germline frameworks (FRs). Briefly, mouse VH was humanized by judicious recruitment of corresponding CDR residues and a few framework (FR) residues into human IGHV1-46*01 or IGHV3-23*01. Mouse VL was humanized by judicious recruitment of corresponding CDR residues and a few framework (FR) residues into human IGKV4-1*01 or IGKV2-28*01. Differences between mouse and the human FR residues were individually modeled to investigate their possible influence on CDR conformation. In order to further humanize the antibody and to increase the binding affinity of the humanized antibodies, residues in CDRs were selected and mutated to the corresponding CDR residues of human germline sequences.

Cell Transfection.

293F cells were cultured under FreeStyle™ 293 Expression Medium (Invitrogen). Transient transfection was performed by co-transfection of expression vectors encoding antibody heavy chain and light chain using 293fectin transfection reagent (Invitrogen), according to the manufacturer's instructions. Four to five days later, supernatants from the transfected cells were harvested and tested for antibody secretion by ELISA. Briefly, 96-well plates (Nunc, Roskilde, Denmark) were coated with 1 ug/ml goat anti-human Fc gamma antibody in phosphate-buffered saline (PBS) for 16 hr at 4° C. After blocking for 1 hr with 0.4% BSA in PBS at room temperature, isolated supernatants were added in 1/3 sequential dilutions, and incubated for 1 hr at room temperature. Plates were subsequently washed three times and incubated with HRP-conjugated goat anti-human kappa-specific antibody for 1 hr at room temperature. After washing, plates were developed with TMB. The reaction was stopped with 2M H2SO4, and OD was measured at 450 nM.

Antibody Purification and Characterization.

The culture supernatant was applied to protein A Sepharose columns (GE Healthcare). The column was washed with PBS, and protein was then eluted with eluting buffer (0.1 M sodium citrate buffer, pH 3.0). Collected fractions were neutralized with 1 M Tris pH 9.0. Finally, purified samples were dialyzed against PBS. Purity of the eluted antibody fraction was analyzed by sodium dodecyl sulfate polyacrylamide gel electrophoresis (SDS-PAGE) on 10% gels under reducing or non-reducing conditions. Bands were visualized by Coomassie brilliant blue staining.

Antigen Binding Activity Measurement by ELISA.

96-well plates (Nunc, Roskilde, Denmark) were coated with 1 ug/ml human c-Kit-Fc fusion protein in phosphate-buffered saline (PBS) for 16 hr at 4° C. After blocking for 1 hr with 0.4% BSA in PBS at room temperature, anti-c-Kit antibodies were added in 1/3 sequential dilutions, and incubated for 1 hr at room temperature. Plates were subsequently washed three times and incubated with HRP-conjugated goat anti-human kappa-specific antibody for 1 hr at room temperature. After washing, plates were developed with TMB. The reaction was stopped with 2M H2504, and OD was measured at 450 nM.

In Vitro Phagocytosis Assay.

MHC-1 cancer cells were washed and counted, then 25 μL containing 1×105 cells in serum-free IMDM were added to each well. Antibody treatment (in 25 μL) with a final concentration of 10 μg/mL was added to the wells and incubated at 37° C. for 30 minutes. At 30 minutes, Macrophages that had previously been harvested with TrypLE were counted and plated with 5×104 cells in 50 μL of serum-free IMDM. Plates were incubated at 37° C. for 2 hours (Effector:Target=1:2). Phagocytosis percentage was calculated by Flow Cytometry analysis looking for GFP+ Macrophages.

ADCC Assay.

Natural killer cells were isolated from human PBMC using EasySep human CD56 positive selection kit from Stemcell Technologies (Vancouver, British Columbia, Canada, catalog #17855). Isolated cells were cultured overnight in RPMI 1640 medium supplement with 10% FBS and 100 U/mL recombinant human IL-2 (PeproTech, Rocky Hill, N.J., catalog #200-02). GIST-T1 cells were labeled with 5 uM Calcein-AM (Thermo Fisher Scientific, Waltham, Mass., catalog #C3100MP) for 10 minutes at 37° C., then washed twice. Anti-c-Kit or isotype control antibody were serially diluted 10-fold from 0.0003 to 30 ug/mL and transferred to a V-bottom assay plate. Labeled GIST-T1 cells were added to the assay plate followed by activated natural killer cells for a final of 1:5 target to effector ratio. After 2 hours incubation, supernatant was collected and transferred to a clean flat bottom plate. Plate were read on SpectraMax M3 fluorescence plate reader with 490 nm excitation, 520 nm emission, and cutoff of 515 nm, with SoftMax Pro 7.0 software. Percent specific lysis was calculated based on relative fluorescence unit (RFU) with the following formula: [(test RFU−mean background RFU)/(mean maximal RFU−mean background RFU)]×100, where background is effector cells+target cells with no antibody, and maximal lysis is effector cells+target cells with lysis buffer. Data were analysis with GraphPad Prism 7.05. Percent specific antibody dependent lysis was plotted against antibody concentration.

HSPC Proliferation Assay.

Frozen cord blood CD34+stem/progenitor cells (ALL-CELLS Catalog #CB005F) were resuspended in HSC retention media, StemSpan SFEMII (STEMCELL technologies Catalog #09605) supplemented with 20 ng/ml of human recombinant SCF (STEMCELL technologies Cat #78062), 20 ng/ml of Recombinant Human Flt3-Ligand (Peprotech Catalog #300-19) and 20 ng/ml of Recombinant Human TPO (Peprotech Catalog #300-18). About 3000 stem cells were plated per well on three COSTAR Ultra low cluster 96-well plates (Corning Catalog #7007). The plates were centrifuged at 1250 rpm at 4° C. for 5 minutes and cells resuspended in 200 ul of HSC retention media with or without the anti-c-Kit antibodies in triplicates. Four anti-c-Kit antibodies, AMG191, AMG191-G1, HF12 and HF112 were tested at concentrations of 0.1, 1, 10 and 50 ug/ml. Cell proliferation was tested using Countbright absolute Counting beads (Invitrogen™ Catalog #C36950) on day 1, 3, 5, and 11. AMG191 has an N to E mutation of position 297 rendering unglycosylated reducing effector function. AMG191-G1 or -IgG1 has a wildtype human IgG1 constant region.

2. Results (a) Anti-c-Kit Hybridoma Variable Region Cloning and Sequencing

An anti-human c-Kit hybridoma cell line was purchased from ATCC (HB-10716). The specificity of the hybridoma clone HB-10716 was examined by ELISA binding to human c-Kit. Heavy and light chain variable regions of HB-10716 were cloned from the hybridoma using universal antibody primers. Multiple clones of each V gene product were sequenced to monitor PCR-induced errors. The nucleotide sequences of VH and VL of HB-10716 were determined, and the deduced amino acid sequences are shown in FIGS. 1A and B, respectively.

(b) Antibody Humanization and CDR Substitutions

To select human antibody frameworks (FRs) to be used as templates for CDR-grafting, the mouse HB-10716 VL and VH regions were compared with those of human germline sequences. The FRs of mouse HB-10716 VL region were found to have higher homology with IGKV4-1 subgroup, and the FRs of the VH region exhibited higher homology with human IGHV1-46 subgroup. The FRs from human IGKV4-1 and IGHV1-46 were therefore used as the bases for designing the humanized HB-10716. Amino acid positions in the FR regions that differ between HB-10716 and IGKV4-1/IGHV1-46 sequences and that may have influence in antigen binding were identified through molecular modeling. Identical residues in the FRs were retained and non-identical residues were either retained or substituted based on the molecular modeling program. Furthermore, residues in the CDR regions of VH and VL were identified via molecular modeling. CDR substitutions were done by site-directed mutagenesis.

Table 2 summaries the new humanized antibodies that were made and their heavy and light chain mature variable region components. In brief, antibodies designated AF have the same variable region frameworks as AMG191. Antibodies designated NF have different variable region frameworks than AMG191. Antibodies designated HF have the same heavy chain variable region framework as AMG191 and a different light chain variable region framework. The CDR substitutions present in each of the chains in Table 2 below relative to the antibody produced by HB-10716 are shown in FIGS. 2A-B and 3A-B.

TABLE 2

| Humanized Antibodies | VH | VL |
| --- | --- | --- |
| AF-2-1 | AH1 | AL2 |
| AF11 | AH2 | AL2 |
| AF12 | AH3 | AL2 |
| AF112 | AH4 | AL2 |
| AF-3 | AH5 | AL2 |
| AF-1-1 | AH4 | AL1 |
| NF | NH | NL |
| NF-2-1 | NH1 | NL2 |
| NF11 | NH2 | NL2 |
| NF12 | NH3 | NL2 |
| NF112 | NH4 | NL2 |
| NF-3 | NH5 | NL2 |
| HF11 | AH3 | NL2 |
| HF12 | AH2 | NL2 |
| HF112 | AH4 | NL2 |

CDR substitutions at H60, H64, and L30 increased the binding either alone or through combination (AF11, AF12, and AF112, Table 2, FIGS. 2A-C). Most importantly, residues at H60 and H64 were mutated back to the human germline sequences, increasing the humanness of the humanized anti-c-Kit antibodies of AF11, AF12, and AF112. Moreover, a single amino acid CDR substitution at H54, H95, or L27 (Table 2, FIGS. 2A-B) impaired the binding of the humanized anti-c-Kit antibodies of AF-2-1, AF-3, and AF-1-1 (FIG. 2D).

An anti-c-Kit humanized antibody, NF, was made by CDR-grafting using different human germline sequences of IGHV3-23*01 and IGKV2-28*01 as the frameworks (Table 2, FIG. 3A-B). Antibody NF showed increased binding activity as compared to AMG191 (FIG. 3C). Then, the same CDR substitutions at H54, H60, H64, H95, L27, and L30 were applied to NF (Table 2, FIG. 3A-B). CDR substitutions at H60, H64, and L30 not only worked with antibodies having IGKV4-1/IGHV1-46 frameworks but also worked with antibodies having IGHV3-23*01/IGKV2-28*01 frameworks. CDR substitutions at H60, H64, and L30 either alone or in combination increased or retained the binding activity of NF11, NF12, and NF112 (FIG. 3D).

Humanized HF11, HF12, and HF112 were constructed by combining different VHs and VLs as shown in Table 2, and they all showed increased binding activities, as compared to AMG191 (FIG. 4).

(c) Humanized Anti-c-Kit Antibodies Promote Macrophage-Mediated Phagocytosis

We next investigated the ability of humanized anti-c-Kit antibodies to enable the phagocytosis of human cancer cells by human peripheral blood-derived macrophages. As AMG191 has a silenced Fc, we made AMG191-G1 which has the same sequences as AMG191, except that AMG191-G1 has an active human IgG1 Fc constant region. AMG191 did not induce phagocytosis as compared to the PBS control; however, AMG191-G1 induced higher phagocytic activity as expected because it has an active human IgG1 scaffold (FIG. 5). AMG191-G1 induced similar levels of phagocytic activity at 0.1, 1, and 10 ug/ml. In contrast to AMG191-G1, humanized AF12, AF112, HF12, HF112, and NF112 were more potent at lower concentration and induced higher phagocytic activity than that of AMG191-G1 at 0.1, 1, or even at 10 ug/ml, suggesting lower therapeutic doses required for humanized AF12, AF112, HF12, HF112, and NF112 (FIG. 5). The data show that while AMG191-G1, AF12, AF112, HF12, HF112, and NF112 are all human IgG1 formatted antibodies, AF12, AF112, HF12, HF112, and NF112 are more potent. It is possibly due to the higher binding affinities of AF12, AF112, HF12, HF112, and NF112 attributed from frameworks and/or CDR substitutions.

(d) Humanized Anti-c-Kit Antibodies Induce Potent ADCC

The ability of humanized anti-c-Kit antibody to induce ADCC activity was tested against GIST cells. AMG191 did not induce ADCC at any of the concentrations tested. HF12 and HF112 mediated ADCC in a dose-dependent manner (FIG. 6).

(e) Humanized Anti-c-Kit Antibodies Inhibit Hematopoietic Stem/Progenitor Cells (HSPC) Proliferation Mature hematopoietic cells develop from hematopoietic stem cells (HSCs) through a hierarchically organized process that produces increasingly lineage-restricted cells with decreasing self-renewing capacity. The cell surface protein tyrosine kinase c-Kit, which interacts with its cognate ligand, stem cell factor (SCF), to regulate HSC self-renewal. By blocking c-Kit interaction with SCF, we tested if humanized anti-c-Kit antibodies can inhibit HSPC proliferation. As shown in FIG. 7, SCF induced HSPC proliferation in the absence of any antibody treatment. However, AMG191, AMG191-G1, HF12, and HF112 inhibited HSPC proliferation (FIG. 7). Moreover, HF12 and HF112 are more potent in inhibiting HSPC proliferation than those of AMG191 and AMG191-G1 (FIG. 7). It is possibly due to the higher binding affinities of HF12 and HF112 attributed from frameworks and/or CDR substitutions.

(f) Humanized Anti-c-Kit does not Induce Significant Mast Cell Degranulation cKIT is expressed on hematopoietic stem cells and mature mast cells. Mast cells are derived from CD34+haematopoietic progenitors in the bone marrow. Upon migration to various peripheral tissues, these progenitor cells differentiate into mature mast cells that express cKIT along with high affinity IgE receptor, FcεRI. Binding of antigen to an IgE primed FcεRI on mast cells triggers degranulation and releasing chemical mediators such as histamine and tryptase along with cytokines, leukotrienes and proteases. The release of chemical mediators causes the classic symptoms of allergy. In clinical use, it is desirable that an anti-cKIT antibody reduce hematopoietic stem cells without inducing mast cell degranulation.

Phenotyped mature mast cells (CD34−, FcεRIα+, cKIT+) differentiated form peripheral whole blood of a healthy human donor were incubated with different concentrations of HF12 and HF12 humanized anti-c-Kit antibodies (10, 1, 0.1 & 0.01 μg/ml) for 7 hrs. A23187 (10 μM) and IgE, plus anti-IgE (10 ug/ml each) were used as positive controls. Degranulation was quantified by measuring the release of β-hexosaminidase using absorbance method as described in the methods.

Human primary mast cells were differentiated in vitro and exhibited the CD34-, FcεRIα+, and cKIT+phenotype at the end of week 9, which was consistent with the phenotypical characteristics of mature mast cells. The cells were then stimulated with calcium ionophore A23187 or IgE in combination with anti-IgE. A23187 and IgE+anti-IgE effectively induced mast cell degranulation as measured by the release of β-hexosaminidase.

Direct treatment of the cells with anti-c-Kit antibodies or cross-linking of anti-c-Kit antibodies by an anti-IgG antibody did not induce significant mast cell degranulation as compared to those of A23187 and anti-IgE treatment (FIG. 8). Immobilization of anti-c-Kit antibodies on a plate also had little effect on mast cell degranulation. Co-incubation of mast cells and NK cells in the presence of various concentrations of anti-c-Kit antibodies also did not induce mast cell degranulation at all concentrations tested.

In conclusion, anti-c-Kit antibodies HF12 and HF112 had little effect on degranulation of primary human mast cells in vitro, as compared to those of calcium ionophore A23187 or IgE in combination with anti-IgE treatment.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the disclosure can be used in combination with any other unless specifically indicated otherwise. Although the present disclosure has been described in some detail by way of illustration and example for purposes of clarity and understanding, it will be apparent that certain changes and modifications may be practiced within the scope of the appended claims.

What is claimed is:

1. An antibody specifically binding to human c-Kit comprising a mature heavy variable region comprising CDRs H1, H2 and H3 as defined by Kabat of SEQ ID NOS:18-20 respectively, and a mature light chain variable region comprising CDRs L1, L2 and L3 as defined by Kabat of SEQ ID NOS:36-38 respectively.

2. The antibody of claim 1, wherein the mature heavy chain variable region shows at least 85% sequence identity to SEQ ID NO:17 and the mature light chain variable region shows at least 85% sequence identity to SEQ ID NO:53, wherein any variation from the indicated SEQ ID NOS. is outside the CDRs as defined by Kabat.

3. The antibody of claim 2, wherein heavy chain position 1 by Kabat numbering is E.

4. The antibody of claim 1, wherein the following positions of the mature light chain variable region are occupied by amino acids as follows:
Position 9 occupied by L,
Position 12 occupied by P,
Position 14 occupied by T,
Position 15 occupied by P,
Position 18 occupied by P,
Position 20 occupied by S,
Position 22 occupied by S,
Position 37 occupied by L,
Position 43 occupied by S,
Position 45 occupied by Q,
Position 74 occupied by K,
Position 77 occupied by R,
Position 78 occupied by V,
Position 79 occupied by E, and
Position 84 occupied by G.

5. The antibody of claim 1, wherein the mature heavy chain variable region has theta sequence of SEQ ID NO:17 except that position 1 can be E, and the mature light chain variable region has a sequence of SEQ ID NO:53.

6. The antibody of claim 1, wherein the mature heavy chain variable region is linked to a heavy chain constant region and the mature light chain variable region is linked to a mature light chain constant region.

7. The antibody of claim 5, wherein the heavy chain constant region is human IgG1.

8. A pharmaceutical composition comprising an antibody of claim 1, and a pharmaceutically acceptable carrier.

9. A method of ablating endogenous HSPCs comprising administering an effective regime of antibody of claim 1 to a subject in need of ablation.

10. A method of treating a cancer expressing c-Kit comprising administering an effective regime of an antibody of claim 1 to a subject having the cancer.

* * * * *

SEQUENCE LISTING

```
<160> NUMBER OF SEQ ID NOS: 54

<210> SEQ ID NO 1
<211> LENGTH: 117
<212> TYPE: PRT
<213> ORGANISM: Artificial sequence
<220> FEATURE:
<223> OTHER INFORMATION: Synthesized

<400> SEQUENCE: 1

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Val Ile Tyr Ser Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Ile Asn Ser Leu Thr Ser Glu Asp Ser Ala Val Tyr Tyr Cys
                85                  90                  95

Ala Arg Glu Arg Asp Thr Arg Phe Gly Asn Trp Gly Gln Gly Thr Leu
            100                 105                 110

Val Thr Val Ser Ala
        115

<210> SEQ ID NO 2
<211> LENGTH: 5
<212> TYPE: PRT
<213> ORGANISM: Artificial sequence
<220> FEATURE:
<223> OTHER INFORMATION: Synthesized
```

<400> SEQUENCE: 2

Ser Tyr Asn Met His
1               5

<210> SEQ ID NO 3
<211> LENGTH: 17
<212> TYPE: PRT
<213> ORGANISM: Artificial sequence
<220> FEATURE:
<223> OTHER INFORMATION: Synthesized

<400> SEQUENCE: 3

Val Ile Tyr Ser Gly Asn Gly Asp Thr Ser Tyr Asn Gln Lys Phe Lys
1               5                   10                  15

Gly

<210> SEQ ID NO 4
<211> LENGTH: 8
<212> TYPE: PRT
<213> ORGANISM: Artificial sequence
<220> FEATURE:
<223> OTHER INFORMATION: Synthesized

<400> SEQUENCE: 4

Glu Arg Asp Thr Arg Phe Gly Asn
1               5

<210> SEQ ID NO 5
<211> LENGTH: 111
<212> TYPE: PRT
<213> ORGANISM: Artificial sequence
<220> FEATURE:
<223> OTHER INFORMATION: Synthesized

<400> SEQUENCE: 5

Asn Ile Val Leu Thr Gln Ser Pro Ala Ser Leu Ala Val Ser Leu Gly
1               5                   10                  15

Leu Arg Ala Thr Ile Ser Cys Arg Ala Ser Glu Ser Val Asp Ile Tyr
                20                  25                  30

Gly Asn Ser Phe Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
        50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Tyr Thr Phe Gly Gly Gly Thr Lys Leu Glu Ile Lys
            100                 105                 110

<210> SEQ ID NO 6
<211> LENGTH: 15
<212> TYPE: PRT
<213> ORGANISM: Artificial sequence
<220> FEATURE:
<223> OTHER INFORMATION: Synthesized

<400> SEQUENCE: 6

Arg Ala Ser Glu Ser Val Asp Ile Tyr Gly Asn Ser Phe Met His
1               5                   10                  15

```
<210> SEQ ID NO 7
<211> LENGTH: 7
<212> TYPE: PRT
<213> ORGANISM: Artificial sequence
<220> FEATURE:
<223> OTHER INFORMATION: Synthesized

<400> SEQUENCE: 7

Leu Ala Ser Asn Leu Glu Ser
1               5

<210> SEQ ID NO 8
<211> LENGTH: 9
<212> TYPE: PRT
<213> ORGANISM: Artificial sequence
<220> FEATURE:
<223> OTHER INFORMATION: Synthesized

<400> SEQUENCE: 8

Gln Gln Asn Asn Glu Asp Pro Tyr Thr
1               5

<210> SEQ ID NO 9
<211> LENGTH: 117
<212> TYPE: PRT
<213> ORGANISM: Artificial sequence
<220> FEATURE:
<223> OTHER INFORMATION: Synthesized

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asn Met His Trp Val Arg Gln Ala Pro Gly Gln Gly Leu Glu Trp Met
            35                  40                  45

Gly Val Ile Tyr Ser Gly Gln Gly Asp Thr Ser Tyr Asn Gln Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Asp Thr Arg Phe Gly Asn Trp Gly Gln Gly Thr Leu
            100                 105                 110

Val Thr Val Ser Ser
        115

<210> SEQ ID NO 10
<211> LENGTH: 5
<212> TYPE: PRT
<213> ORGANISM: Artificial sequence
<220> FEATURE:
<223> OTHER INFORMATION: Synthesized

<400> SEQUENCE: 10

Ser Tyr Asn Met His
1               5

<210> SEQ ID NO 11
<211> LENGTH: 17
<212> TYPE: PRT
<213> ORGANISM: Artificial sequence
<220> FEATURE:
<223> OTHER INFORMATION: Synthesized
```

<400> SEQUENCE: 11

Val Ile Tyr Ser Gly Gln Gly Asp Thr Ser Tyr Asn Gln Lys Phe Lys
1               5                   10                  15

Gly

<210> SEQ ID NO 12
<211> LENGTH: 8
<212> TYPE: PRT
<213> ORGANISM: Artificial sequence
<220> FEATURE:
<223> OTHER INFORMATION: Synthesized

<400> SEQUENCE: 12

Glu Arg Asp Thr Arg Phe Gly Asn
1               5

<210> SEQ ID NO 13
<211> LENGTH: 117
<212> TYPE: PRT
<213> ORGANISM: Artificial sequence
<220> FEATURE:
<223> OTHER INFORMATION: Synthesized

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Met
        35                  40                  45

Gly Val Ile Tyr Ser Gly Asn Gly Asp Thr Ser Tyr Ala Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Asp Thr Arg Phe Gly Asn Trp Gly Gln Gly Thr Leu
            100                 105                 110

Val Thr Val Ser Ser
        115

<210> SEQ ID NO 14
<211> LENGTH: 5
<212> TYPE: PRT
<213> ORGANISM: Artificial sequence
<220> FEATURE:
<223> OTHER INFORMATION: Synthesized

<400> SEQUENCE: 14

Ser Tyr Asn Met His
1               5

<210> SEQ ID NO 15
<211> LENGTH: 17
<212> TYPE: PRT
<213> ORGANISM: Artificial sequence
<220> FEATURE:
<223> OTHER INFORMATION: Synthesized

<400> SEQUENCE: 15

Val Ile Tyr Ser Gly Asn Gly Asp Thr Ser Tyr Ala Gln Lys Phe Lys

Gly

<210> SEQ ID NO 16
<211> LENGTH: 8
<212> TYPE: PRT
<213> ORGANISM: Artificial sequence
<220> FEATURE:
<223> OTHER INFORMATION: Synthesized

<400> SEQUENCE: 16

Glu Arg Asp Thr Arg Phe Gly Asn
1               5

<210> SEQ ID NO 17
<211> LENGTH: 117
<212> TYPE: PRT
<213> ORGANISM: Artificial sequence
<220> FEATURE:
<223> OTHER INFORMATION: Synthesized

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Met
        35                  40                  45

Gly Val Ile Tyr Ser Gly Asn Gly Asp Thr Ser Tyr Asn Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Asp Thr Arg Phe Gly Asn Trp Gly Gln Gly Thr Leu
            100                 105                 110

Val Thr Val Ser Ser
        115

<210> SEQ ID NO 18
<211> LENGTH: 5
<212> TYPE: PRT
<213> ORGANISM: Artificial sequence
<220> FEATURE:
<223> OTHER INFORMATION: Synthesized

<400> SEQUENCE: 18

Ser Tyr Asn Met His
1               5

<210> SEQ ID NO 19
<211> LENGTH: 17
<212> TYPE: PRT
<213> ORGANISM: Artificial sequence
<220> FEATURE:
<223> OTHER INFORMATION: Synthesized

<400> SEQUENCE: 19

Val Ile Tyr Ser Gly Asn Gly Asp Thr Ser Tyr Asn Gln Lys Phe Gln
1               5                   10                  15

Gly

```
<210> SEQ ID NO 20
<211> LENGTH: 8
<212> TYPE: PRT
<213> ORGANISM: Artificial sequence
<220> FEATURE:
<223> OTHER INFORMATION: Synthesized

<400> SEQUENCE: 20

Glu Arg Asp Thr Arg Phe Gly Asn
1               5

<210> SEQ ID NO 21
<211> LENGTH: 117
<212> TYPE: PRT
<213> ORGANISM: Artificial sequence
<220> FEATURE:
<223> OTHER INFORMATION: Synthesized

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asn Met His Trp Val Arg Gln Ala Pro Gly Gln Gly Leu Glu Trp Met
            35                  40                  45

Gly Val Ile Tyr Ser Gly Asn Gly Asp Thr Ser Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Asp Thr Arg Phe Gly Asn Trp Gly Gln Gly Thr Leu
            100                 105                 110

Val Thr Val Ser Ser
        115

<210> SEQ ID NO 22
<211> LENGTH: 5
<212> TYPE: PRT
<213> ORGANISM: Artificial sequence
<220> FEATURE:
<223> OTHER INFORMATION: Synthesized

<400> SEQUENCE: 22

Ser Tyr Asn Met His
1               5

<210> SEQ ID NO 23
<211> LENGTH: 17
<212> TYPE: PRT
<213> ORGANISM: Artificial sequence
<220> FEATURE:
<223> OTHER INFORMATION: Synthesized

<400> SEQUENCE: 23

Val Ile Tyr Ser Gly Asn Gly Asp Thr Ser Tyr Ala Gln Lys Phe Gln
1               5                   10                  15

Gly

<210> SEQ ID NO 24
<211> LENGTH: 8
<212> TYPE: PRT
```

```
<213> ORGANISM: Artificial sequence
<220> FEATURE:
<223> OTHER INFORMATION: Synthesized

<400> SEQUENCE: 24

Glu Arg Asp Thr Arg Phe Gly Asn
1               5

<210> SEQ ID NO 25
<211> LENGTH: 117
<212> TYPE: PRT
<213> ORGANISM: Artificial sequence
<220> FEATURE:
<223> OTHER INFORMATION: Synthesized

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Met
        35                  40                  45

Gly Val Ile Tyr Ser Gly Asn Gly Asp Thr Ser Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Arg Asp Thr Arg Phe Gly Asn Trp Gly Gln Gly Thr Leu
            100                 105                 110

Val Thr Val Ser Ser
        115

<210> SEQ ID NO 26
<211> LENGTH: 5
<212> TYPE: PRT
<213> ORGANISM: Artificial sequence
<220> FEATURE:
<223> OTHER INFORMATION: Synthesized

<400> SEQUENCE: 26

Ser Tyr Asn Met His
1               5

<210> SEQ ID NO 27
<211> LENGTH: 17
<212> TYPE: PRT
<213> ORGANISM: Artificial sequence
<220> FEATURE:
<223> OTHER INFORMATION: Synthesized

<400> SEQUENCE: 27

Val Ile Tyr Ser Gly Asn Gly Asp Thr Ser Tyr Asn Gln Lys Phe Lys
1               5                   10                  15

Gly

<210> SEQ ID NO 28
<211> LENGTH: 8
<212> TYPE: PRT
<213> ORGANISM: Artificial sequence
<220> FEATURE:
<223> OTHER INFORMATION: Synthesized
```

<400> SEQUENCE: 28

Asp Arg Asp Thr Arg Phe Gly Asn
1               5

<210> SEQ ID NO 29
<211> LENGTH: 117
<212> TYPE: PRT
<213> ORGANISM: Artificial sequence
<220> FEATURE:
<223> OTHER INFORMATION: Synthesized

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asn Met His Trp Val Arg Gln Ala Pro Gly Gln Gly Leu Glu Trp Met
            35                  40                  45

Gly Val Ile Tyr Ser Gly Asn Gly Asp Thr Ser Tyr Asn Gln Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Asp Thr Arg Phe Gly Asn Trp Gly Gln Gly Thr Leu
            100                 105                 110

Val Thr Val Ser Ser
        115

<210> SEQ ID NO 30
<211> LENGTH: 98
<212> TYPE: PRT
<213> ORGANISM: Homo sapiens

<400> SEQUENCE: 30

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 31
<211> LENGTH: 111
<212> TYPE: PRT
<213> ORGANISM: Artificial sequence
<220> FEATURE:
<223> OTHER INFORMATION: Synthesized

<400> SEQUENCE: 31

Asp Ile Val Met Thr Gln Ser Pro Asp Ser Leu Ala Val Ser Leu Gly
1               5                   10                  15

Glu Arg Ala Thr Ile Asn Cys Arg Ala Ser Asp Ser Val Asp Ile Tyr
                    20                  25                  30

Gly Asn Ser Phe Met His Trp Tyr Gln Gln Lys Pro Gly Gln Pro Pro
                35                  40                  45

Lys Leu Leu Ile Tyr Leu Ala Ser Asn Leu Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Asn Asn
                85                  90                  95

Glu Asp Pro Tyr Thr Phe Gly Gly Gly Thr Lys Val Glu Ile Lys
                100                 105                 110

<210> SEQ ID NO 32
<211> LENGTH: 15
<212> TYPE: PRT
<213> ORGANISM: Artificial sequence
<220> FEATURE:
<223> OTHER INFORMATION: Synthesized

<400> SEQUENCE: 32

Arg Ala Ser Asp Ser Val Asp Ile Tyr Gly Asn Ser Phe Met His
1               5                   10                  15

<210> SEQ ID NO 33
<211> LENGTH: 7
<212> TYPE: PRT
<213> ORGANISM: Artificial sequence
<220> FEATURE:
<223> OTHER INFORMATION: Synthesized

<400> SEQUENCE: 33

Leu Ala Ser Asn Leu Glu Ser
1               5

<210> SEQ ID NO 34
<211> LENGTH: 9
<212> TYPE: PRT
<213> ORGANISM: Artificial sequence
<220> FEATURE:
<223> OTHER INFORMATION: Synthesized

<400> SEQUENCE: 34

Gln Gln Asn Asn Glu Asp Pro Tyr Thr
1               5

<210> SEQ ID NO 35
<211> LENGTH: 111
<212> TYPE: PRT
<213> ORGANISM: Artificial sequence
<220> FEATURE:
<223> OTHER INFORMATION: Synthesized

<400> SEQUENCE: 35

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Ile Tyr
                    20                  25                  30

Gly Gln Ser Phe Met His Trp Tyr Gln Gln Lys Pro Gly Gln Pro Pro
                35                  40                  45

Lys Leu Leu Ile Tyr Leu Ala Ser Asn Leu Glu Ser Gly Val Pro Asp
 50                  55                  60

```
Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Asn Asn
                 85                  90                  95

Glu Asp Pro Tyr Thr Phe Gly Gly Gly Thr Lys Val Glu Ile Lys
            100                 105                 110

<210> SEQ ID NO 36
<211> LENGTH: 15
<212> TYPE: PRT
<213> ORGANISM: Artificial sequence
<220> FEATURE:
<223> OTHER INFORMATION: Synthesized

<400> SEQUENCE: 36

Arg Ala Ser Glu Ser Val Asp Ile Tyr Gly Gln Ser Phe Met His
 1               5                  10                  15

<210> SEQ ID NO 37
<211> LENGTH: 7
<212> TYPE: PRT
<213> ORGANISM: Artificial sequence
<220> FEATURE:
<223> OTHER INFORMATION: Synthesized

<400> SEQUENCE: 37

Leu Ala Ser Asn Leu Glu Ser
 1               5

<210> SEQ ID NO 38
<211> LENGTH: 9
<212> TYPE: PRT
<213> ORGANISM: Artificial sequence
<220> FEATURE:
<223> OTHER INFORMATION: Synthesized

<400> SEQUENCE: 38

Gln Gln Asn Asn Glu Asp Pro Tyr Thr
 1               5

<210> SEQ ID NO 39
<211> LENGTH: 111
<212> TYPE: PRT
<213> ORGANISM: Artificial sequence
<220> FEATURE:
<223> OTHER INFORMATION: Synthesized

<400> SEQUENCE: 39

Asp Ile Val Met Thr Gln Ser Pro Asp Ser Leu Ala Val Ser Leu Gly
 1               5                  10                  15

Glu Arg Ala Thr Ile Asn Cys Arg Ala Ser Glu Ser Val Asp Ile Tyr
                 20                  25                  30

Gly Asn Ser Phe Met His Trp Tyr Gln Gln Lys Pro Gly Gln Pro Pro
             35                  40                  45

Lys Leu Leu Ile Tyr Leu Ala Ser Asn Leu Glu Ser Gly Val Pro Asp
     50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Asn Asn
                 85                  90                  95

Glu Asp Pro Tyr Thr Phe Gly Gly Gly Thr Lys Val Glu Ile Lys
            100                 105                 110
```

<210> SEQ ID NO 40
<211> LENGTH: 101
<212> TYPE: PRT
<213> ORGANISM: Homo sapiens

<400> SEQUENCE: 40

```
Asp Ile Val Met Thr Gln Ser Pro Asp Ser Leu Ala Val Ser Leu Gly
1               5                   10                  15

Glu Arg Ala Thr Ile Asn Cys Lys Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro
            100
```

<210> SEQ ID NO 41
<211> LENGTH: 17
<212> TYPE: PRT
<213> ORGANISM: Homo sapiens

<400> SEQUENCE: 41

```
Lys Ser Ser Gln Ser Val Leu Tyr Ser Asn Asn Lys Asn Tyr Leu
1               5                   10                  15

Ala
```

<210> SEQ ID NO 42
<211> LENGTH: 7
<212> TYPE: PRT
<213> ORGANISM: Homo sapiens

<400> SEQUENCE: 42

```
Trp Ala Ser Thr Arg Glu Ser
1               5
```

<210> SEQ ID NO 43
<211> LENGTH: 7
<212> TYPE: PRT
<213> ORGANISM: Homo sapiens

<400> SEQUENCE: 43

```
Gln Gln Tyr Tyr Ser Thr Pro
1               5
```

<210> SEQ ID NO 44
<211> LENGTH: 117
<212> TYPE: PRT
<213> ORGANISM: Artificial sequence
<220> FEATURE:
<223> OTHER INFORMATION: Synthesized

<400> SEQUENCE: 44

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
```

```
                    20                  25                  30

Asn Met His Trp Val Arg Gln Ala Pro Gly Lys Gly Leu Glu Trp Val
        35                  40                  45

Gly Val Ile Tyr Ser Gly Asn Gly Asp Thr Ser Tyr Asn Gln Lys Phe
    50                  55                  60

Lys Gly Arg Phe Thr Ile Ser Ala Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Arg Asp Thr Arg Phe Gly Asn Trp Gly Gln Gly Thr Leu
            100                 105                 110

Val Thr Val Ser Ser
        115

<210> SEQ ID NO 45
<211> LENGTH: 117
<212> TYPE: PRT
<213> ORGANISM: Artificial sequence
<220> FEATURE:
<223> OTHER INFORMATION: Synthesized

<400> SEQUENCE: 45

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
                20                  25                  30

Asn Met His Trp Val Arg Gln Ala Pro Gly Lys Gly Leu Glu Trp Val
        35                  40                  45

Gly Val Ile Tyr Ser Gly Gln Gly Asp Thr Ser Tyr Asn Gln Lys Phe
    50                  55                  60

Lys Gly Arg Phe Thr Ile Ser Ala Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Arg Asp Thr Arg Phe Gly Asn Trp Gly Gln Gly Thr Leu
            100                 105                 110

Val Thr Val Ser Ser
        115

<210> SEQ ID NO 46
<211> LENGTH: 117
<212> TYPE: PRT
<213> ORGANISM: Artificial sequence
<220> FEATURE:
<223> OTHER INFORMATION: Synthesized

<400> SEQUENCE: 46

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
                20                  25                  30

Asn Met His Trp Val Arg Gln Ala Pro Gly Lys Gly Leu Glu Trp Val
        35                  40                  45

Gly Val Ile Tyr Ser Gly Asn Gly Asp Thr Ser Tyr Ala Gln Lys Phe
    50                  55                  60

Lys Gly Arg Phe Thr Ile Ser Ala Asp Lys Ser Lys Asn Thr Ala Tyr
65                  70                  75                  80
```

Leu Gln Met Asn Ser Leu Arg Ala Glu Asp Thr Ala Val Tyr Tyr Cys
                85                  90                  95

Ala Arg Glu Arg Asp Thr Arg Phe Gly Asn Trp Gly Gln Gly Thr Leu
            100                 105                 110

Val Thr Val Ser Ser
            115

<210> SEQ ID NO 47
<211> LENGTH: 117
<212> TYPE: PRT
<213> ORGANISM: Artificial sequence
<220> FEATURE:
<223> OTHER INFORMATION: Synthesized

<400> SEQUENCE: 47

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Asn Met His Trp Val Arg Gln Ala Pro Gly Lys Gly Leu Glu Trp Val
        35                  40                  45

Gly Val Ile Tyr Ser Gly Asn Gly Asp Thr Ser Tyr Asn Gln Lys Phe
    50                  55                  60

Gln Gly Arg Phe Thr Ile Ser Ala Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Arg Asp Thr Arg Phe Gly Asn Trp Gly Gln Gly Thr Leu
            100                 105                 110

Val Thr Val Ser Ser
            115

<210> SEQ ID NO 48
<211> LENGTH: 117
<212> TYPE: PRT
<213> ORGANISM: Artificial sequence
<220> FEATURE:
<223> OTHER INFORMATION: Synthesized

<400> SEQUENCE: 48

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Asn Met His Trp Val Arg Gln Ala Pro Gly Lys Gly Leu Glu Trp Val
        35                  40                  45

Gly Val Ile Tyr Ser Gly Asn Gly Asp Thr Ser Tyr Ala Gln Lys Phe
    50                  55                  60

Gln Gly Arg Phe Thr Ile Ser Ala Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Arg Asp Thr Arg Phe Gly Asn Trp Gly Gln Gly Thr Leu
            100                 105                 110

Val Thr Val Ser Ser
            115

<210> SEQ ID NO 49

```
<211> LENGTH: 117
<212> TYPE: PRT
<213> ORGANISM: Artificial sequence
<220> FEATURE:
<223> OTHER INFORMATION: Synthesized

<400> SEQUENCE: 49

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Asn Met His Trp Val Arg Gln Ala Pro Gly Lys Gly Leu Glu Trp Val
        35                  40                  45

Gly Val Ile Tyr Ser Gly Asn Gly Asp Thr Ser Tyr Asn Gln Lys Phe
    50                  55                  60

Lys Gly Arg Phe Thr Ile Ser Ala Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Arg Asp Thr Arg Phe Gly Asn Trp Gly Gln Gly Thr Leu
            100                 105                 110

Val Thr Val Ser Ser
        115

<210> SEQ ID NO 50
<211> LENGTH: 98
<212> TYPE: PRT
<213> ORGANISM: Homo sapiens

<400> SEQUENCE: 50

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 51
<211> LENGTH: 111
<212> TYPE: PRT
<213> ORGANISM: Artificial sequence
<220> FEATURE:
<223> OTHER INFORMATION: Synthesized

<400> SEQUENCE: 51

Asp Ile Val Met Thr Gln Ser Pro Leu Ser Leu Pro Val Thr Pro Gly
1               5                   10                  15

Glu Pro Ala Ser Ile Ser Cys Arg Ala Ser Glu Ser Val Asp Ile Tyr
            20                  25                  30

Gly Asn Ser Phe Met His Trp Tyr Leu Gln Lys Pro Gly Gln Ser Pro
        35                  40                  45
```

Gln Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Asn Asn
                85                  90                  95

Glu Asp Pro Tyr Thr Phe Gly Gly Gly Thr Lys Val Glu Ile Lys
            100                 105                 110

<210> SEQ ID NO 52
<211> LENGTH: 111
<212> TYPE: PRT
<213> ORGANISM: Artificial sequence
<220> FEATURE:
<223> OTHER INFORMATION: Synthesized

<400> SEQUENCE: 52

Asp Ile Val Met Thr Gln Ser Pro Leu Ser Leu Pro Val Thr Pro Gly
1               5                   10                  15

Glu Pro Ala Ser Ile Ser Cys Arg Ala Ser Asp Ser Val Asp Ile Tyr
                20                  25                  30

Gly Asn Ser Phe Met His Trp Tyr Leu Gln Lys Pro Gly Gln Ser Pro
            35                  40                  45

Gln Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Asn Asn
                85                  90                  95

Glu Asp Pro Tyr Thr Phe Gly Gly Gly Thr Lys Val Glu Ile Lys
            100                 105                 110

<210> SEQ ID NO 53
<211> LENGTH: 111
<212> TYPE: PRT
<213> ORGANISM: Artificial sequence
<220> FEATURE:
<223> OTHER INFORMATION: Synthesized

<400> SEQUENCE: 53

Asp Ile Val Met Thr Gln Ser Pro Leu Ser Leu Pro Val Thr Pro Gly
1               5                   10                  15

Glu Pro Ala Ser Ile Ser Cys Arg Ala Ser Glu Ser Val Asp Ile Tyr
                20                  25                  30

Gly Gln Ser Phe Met His Trp Tyr Leu Gln Lys Pro Gly Gln Ser Pro
            35                  40                  45

Gln Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Asn Asn
                85                  90                  95

Glu Asp Pro Tyr Thr Phe Gly Gly Gly Thr Lys Val Glu Ile Lys
            100                 105                 110

<210> SEQ ID NO 54
<211> LENGTH: 100
<212> TYPE: PRT
<213> ORGANISM: Homo sapiens

```
<400> SEQUENCE: 54

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
            85                  90                  95

Leu Gln Thr Pro
            100
```